US009346856B2

(12) United States Patent
Pascon et al.

(10) Patent No.: US 9,346,856 B2
(45) Date of Patent: May 24, 2016

(54) ISOLATED NUCLEIC ACID MOLECULES FROM THE GENOME OF CITRUS LEPROSIS VIRUS AND USES THEREOF

(75) Inventors: Renata Castiglioni Pascon, Campinas (BR); Ana Claudia Rasera Silva, Campinas (BR)

(73) Assignee: MONSANTO DO BRASIL LTDA., Sao Paulo (BR)

( * ) Notice: Subject to any disclaimer, the term of this patent is extended or adjusted under 35 U.S.C. 154(b) by 0 days.

(21) Appl. No.: 13/079,090

(22) Filed: Apr. 4, 2011

(65) Prior Publication Data

US 2011/0283426 A1  Nov. 17, 2011

Related U.S. Application Data

(62) Division of application No. 11/664,926, filed as application No. PCT/BR2005/000180 on Sep. 6, 2005, now Pat. No. 7,943,339.

(60) Provisional application No. 60/620,169, filed on Oct. 18, 2004, provisional application No. 60/629,866, filed on Nov. 19, 2004, provisional application No. 60/633,921, filed on Dec. 6, 2004, provisional application No. 60/641,335, filed on Jan. 4, 2005, provisional application No. 60/651,828, filed on Feb. 10, 2005.

(51) Int. Cl.
*A01H 5/00* (2006.01)
*C07K 14/005* (2006.01)
*C12Q 1/70* (2006.01)

(52) U.S. Cl.
CPC ............. *C07K 14/005* (2013.01); *C12Q 1/701* (2013.01); *C12N 2760/20022* (2013.01)

(58) Field of Classification Search
CPC .................. C07K 14/005; C12N 2760/20022; C12Q 1/701
USPC ........................................................ 800/301
See application file for complete search history.

(56) References Cited

PUBLICATIONS

Locali et al. Nov. 2003, Plant Disease 87:1317-1321.*
Fourgoux-Nicol et al 1999, Plant Molecular Biology 40 :857-872.*
Citrus Disease, Nov. 2011.*
Eliane Cristina Locali et al., "Development of a Molecular Tool for the Diagnosis of Leprosis, a Major Threat to Citris Production in the Americas", Plant Disease, Nov. 2003, vol. 87, pp. 1317-1321.
E.W. Kitajima et al., "Brevipalpus—transmitted plant virus-like diseases: cytopathology and some recent cases", Experimental and Applied Acarology 30: 135-160, 2003.
J.C.V. Rodrigues et al., "Citrus leprosis virus vectored by *Brevipalpus phoenicis* (Acari: Tenuipalpidae) on citrus in Brazil", Experimental and Applied Acarology 30: 161-179, 2003.
E.C. Locali-Fabris at al., "Complete nucleotide sequence, genomic organization and phylogenetic analysis of Citrus leprosies virus cytoplasmic type", Journal of General Virology (2006) 87, 2721-2729.
Renata C. Pascon et al., "The complete nucleotide sequence and genomic organization of Citrus Leprosis associated Virus, Cytoplasmic type (CiLV-C)", Virus Genes (2006) 32:289-298.
Non-Final Office Action U.S. Appl. No. 11/664,926 dated Jan. 21, 2010.
Locali et al., 2003, Plant Disease 87:1317-1321.
Non-Final Office Action U.S. Appl. No. 11/664,926 dated Jul. 21, 2010.
Fourgoux-Nicol et al., 1999, Plant Molecular Biology 40:857-872.
Notice of Allowance U.S. Appl. No. 11/664,926 dated Jan. 6, 2011.

* cited by examiner

*Primary Examiner* — Li Zheng
(74) *Attorney, Agent, or Firm* — Hauptman Ham, LLP

(57) ABSTRACT

The present disclosure embraces nucleic acid molecules found in the genome of the *Citrus* Leprosis Virus (CiLV), which is associated to *Citrus* Leprosis (CiL) disease. The cloned CiLV nucleic acid molecules can be used as probes or can be used to design oligonucleotide primers for detecting CiLV in biological samples, particularly leaves, roots and other tissues or organs of plants, such as plants from the genera *Citrus* and *Poncirus*. The cloned CiLV nucleic acid molecules are expressed in cells to provide immunogenic proteins for raising antibodies against CiLV, which can then be used to detect CiLV in biological samples. It also comprises the nucleic acid molecules represented in SEQ ID Nos. 5 and 8, in whole or part, as well as transgenic plants, such as monocots and dicots, containing the CiLV nucleic acid molecules, in any kind of combination, so that expression increases resistance to CiL disease.

20 Claims, 3 Drawing Sheets

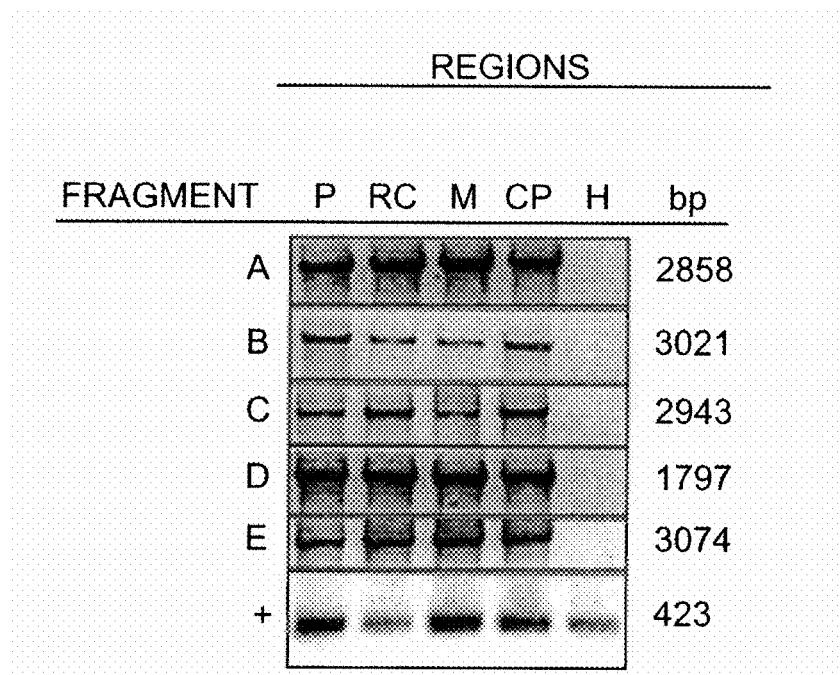
FIG. 1B
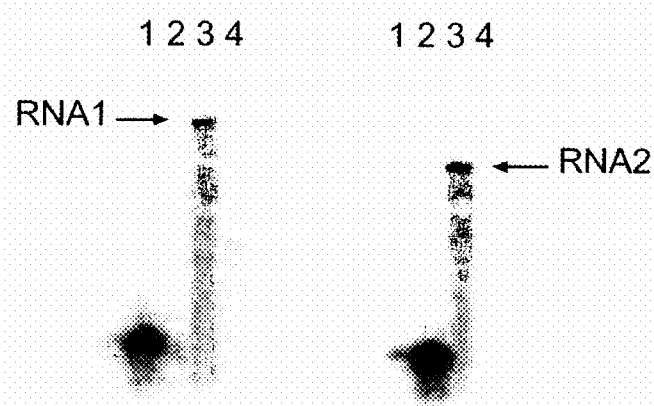
FIG. 2A  FIG. 2B

ISOLATED NUCLEIC ACID MOLECULES FROM THE GENOME OF CITRUS LEPROSIS VIRUS AND USES THEREOF

CROSS-REFERENCE TO RELATED APPLICATION

This application is a divisional of U.S. application Ser. No. 11/664,936 (now U.S. Pat. No. 7,943,339), filed Apr. 5, 2007, which is a national stage of PCT/BR2005/00180, filed Sep. 6, 2005 and published in English, and claims the benefit of U.S. Provisional Application Nos. 60/651,828, filed Feb. 10, 2005; 60/641,335, filed Jan. 4, 2005; 60/633,921, filed Dec. 6, 2004; 60/629,866, filed Nov. 19, 2004, and 60/620,169, filed Oct. 18, 2004. Each application is incorporated herein in its entirety.

FIELD OF THE INVENTION

The invention relates generally to the fields of molecular biology, biochemistry, plant pathology, and agriculture. More particularly, the invention relates to nucleic acid molecules and proteins from a phytopathogenic virus, which are suitable for disease diagnosis, treatment of plant pathologies and generation of virus resistant transgenic plants.

BACKGROUND AND PRIOR ART

*Citrus* diseases caused by viruses lead to significant economical loss worldwide (Derrick, K. S. and Timmer, L. W., Annu. Rev. Phytopathol., 38:181-205 (2000)). One example of a disease causing virus is *Citrus* Tristeza Virus (CTV), a member of the *Closterovirus* group, which induces serious disease syndromes in *citrus*, including quick decline resulting in death of trees on sour orange rootstock, and stem pitting of scion cultivars regardless of the rootstock used (Bar-Joseph et al., Annu. Rev. Phytopathol. 27:291-316 (1989)).

In 1937, millions of sweet orange trees grafted on to sour orange rootstocks were lost in Brazil, due to *citrus* tristeza. The exchange of sour orange stock by Rangpur lime rootstock solved this problem (Gimenes-Fernandes, N. and Bassanezi, R. B. Summa, Phytopathologica., 27:93 (2001)).

In addition to CTV, other disease causing viruses are economically important. For example, CSDV causes citrus tree (sweet orange) death a few months after symptom detection (Gimenes-Femandes, N. and Bassanezi, R. B. Summa Phytopathologica., 27:93 (2001)). The disease is associated with the presence of a *Tymovirus* in symptomatic trees and it is believed to be carried by an insect vector (Maccheroni Jr. et al, Journal of Virology, 79(5):3028-37 (2005)).

*Citrus* leprosis (CiL) is another economically relevant virus related disease, especially in the State of São Paulo, the largest *citrus* producing area in Brazil, where the disease is endemic. CiL is also starting to move to Central American countries, including Guatemala, Honduras, Costa Rica and Panama (Dominguez, F. S.; Bandel, A.; Childers, C; Kitajima, E. W. Plant Disease, 85:228 (2001)). CiL is vectored by mites from the *Brevipalpus* genus which transmit a virus herein designated *Citrus* leprosis virus (CiLV), and usually affects sweet orange (Rodriguez, J. C.; Kitajima, E. W.; Childers, C. C.; Chagas, C. M. Exp and Appl Acarol, 30:161-79 (2003)). The symptoms related to this disease include circular clorotic lesions on both sides of the leaf. Eventually, the lesions become necrotic, assuming a central brownish color, leading to defoliation. Lesions are also present on branches and fruits, causing severe fruit damage and drop, leading to serious tree decline. Apart from sweet orange trees, which are very susceptible to CiL, the CiL symptoms can affect other varieties such as tangerine, but the susceptibility to the virus can vary from resistant to tolerant depending on the *citrus* variety. Mechanical transmission of CiLV can be achieved successfully from *citrus* to *citrus*, and from *citrus* to herbaceous plants (e.g., *Chenopodium amaranticolor, C. quinoa* and *Gomphrena globosa*) using lesion extracts (Colariccio, A.; Lovisolo, O.; Chagas, C. M.; Galetti, S. R.; Rossetti, V.; Kitajima, E. W. Fitopatol. Bras., 20:208-213 (1995)).

CiLV has been found in two different forms. Under electron microscopy, CiLV can be seen as rod shaped, enveloped particules, 30-40 nm×110-130 nm in size, present in the cytoplasm of leaf tissues (Kitajima, E. W.; Muller, G. W.; Costa, A. S.; Yuri, W. Virology, 50:254-258 (1972)). In another report, similarly sized and shaped particles were found in the nucleus; however these were not surrounded by an envelope (Colariccio, A.; Lovisolo, O.; Chagas, C. M.; Galetti, S. R.; Rossetti, V.; Kitajima, E. W. Fitopatol. Bras., 20:208-213 (1995)). Based on the morphology and occurrence of the two forms, CiLV has been classified as a Rhabdovirus.

Recently, Locali et al. (Plant Disease, 87:1317-1321 (2003)) were able to isolate some CiLV sequences using RT-PCR from RNA samples prepared from symptomatic leaves.

The control of CiL is currently carried out with acaricides, which exterminate the vector, *Brevipalpus phaenicis*; however, expenditures directed to exterminating this mite cost over 100 million dollars every year. (Rodriguez, J. C.; Kitajima, E. W.; Childers, C. C.; Chagas, C. M. Exp and Appl Acarol, 30:161-79 (2003)). This figure represents 80% of the total expenses relating to defenses against the pest. Therefore, there is the need to improve the means to control this disease that is both cost effective and efficient. Also, there is a worldwide concern to reduce the amount of toxic products, such as acaricides, which pollute the environment.

In order to explore the possibility of using alternative ways to control CiL that are economically sound and do not involve environmentally toxic compounds, a program to sequence the genome of CiLV was established. Several approaches were used to sequence the genome of this virus. Initially, short specific sequences from the Replicase (402 bp) and Movement Protein (MP) (339 bp) genes were obtained from symptomatic leaves of sweet orange, using diagnostic RT-PCR and gene specific primers MP-F (5' GCGTATTGGCGTTGGATTTCTGAC 3') (SEQ ID NO: 1) and MP-R (5' TGTATACCAAGCCGCCTGTGAACT 3') (SEQ ID NO: 2) for the Movement Protein and REP-F (5' GATACGGGACGCATAACA 3') (SEQ ID NO: 3) and REP-R (5' TTCTGGCTCAACATCTGG 3') (SEQ ID NO: 4) for the Replicase (Locali, E. C.; Freitas-Astua, J.; Takita, M. A.; Astua-Monge, G.; Antoniolli, R.; Kitajima, E. W.; Machado, M. A. Plant Disease, 87:1317-1321 (2003)). These sequences were used as templates to design primers to extend these regions and obtain more virus sequences toward the 5' and 3' regions of the two genes. Another approach was the construction of a subtractive library. In this technique, polyA RNA from symptomatic and asymptomatic leaves were extracted and converted into cDNA, separately. These cDNAs were hybridized to each other at specific temperature and salt concentrations and amplified by PCR in such a way that only the sequences specific to the symptomatic leaves were amplified. The remaining cDNA sequences that are common to both cDNA populations were not amplified and therefore lost. The subtracted PCR amplified sequences were cloned and sequenced to search for virus sequences. Also, the subtractive library was enriched for viral sequences using primers based on the viral sequences obtained by the RT-PCR in the first experiment described above. The combination of these 2 approaches generated the complete sequence of the CiLV genome, which is a bipartite virus, i.e., one that presents two RNA segments. The nucleotide sequence of RNA1 is 8730 bp long (SEQ ID NO: 5). One large ORF of 7539 bp, starting with an AUG codon at position 108-110 and terminating with an UAA codon at 7644-7646, was detected. This ORF encodes a 2512 amino acid replicase protein (with an estimated molecular weight of 286.4 KDa) (SEQ ID NO: 6) with sequence similarities to other replicases from plant viruses, especially the Furovirus. The following domains are present in the polyprotein: i) a methyl transferase, from residues 128 to 325; ii) a putative protease comprising amino acids 683 to 803; iii) a helicase, from amino acid 1521 to amino acid 1697 and iv) a RNA-dependent RNA polymerase domain comprising amino acid 2221 to 2458. All numbering refers to SEQ. ID. NO: 6. There is a second ORF (792 bp), in RNA1, starting at position 7709-7711 (AUG) and terminating at 8498-8500 (UAG). It encodes a putative 263 amino acid polypeptide (with an estimated molecular weight of 29.1 KDa) (SEQ ID NO: 7), herein called p29. This polypeptide has 32% identity to Sindbis virus capsid protein. RNA1 has 107 nucleotide long 5' UTR (1 to 107) and a 230 nucleotide 3' UTR (position 8501 to 8730), excluding its polyA tail.

The sequence of RNA2 is 4975 bps long (SEQ ID NO: 8), and contains 4 putative ORFs. The first one, closest to the 5' end, "p15", is 393 nucleotide long (AUG at position 67 and UAA at 459), encoding a 130 amino acid polypeptide (SEQ ID NO: 9). This polypeptide has 21% identity to an envelope glycoprotein from Human Immunodeficiency Virus-1 (Yamaguchi, Y., Delehouzee, S., Handa, H. Microbes Infect. 4, 1169-75 (2002)). The second ORF, "p61", comprises 1614 nucleotides, starting at 1590 (AUG) and terminating at 3203 (UAA), encoding a 537 amino acid polypeptide (SEQ ID NO: 10). This polypeptide has 23% identity to a *Saccharomyces cerevisiae* mannosyltransferase KTR4. The third ORF (p32) is 894 nucleotide long, with its start codon at position 3228 (AUG) and stop codon at 4121 (UAA). It encodes a 297 amino acid polypeptide with an estimated molecular weight of 32.5 KDa (SEQ ID NO: 11). Similarity searches at the NCBI GenBank showed significant homology to movement proteins of plant viruses (E value=7e-09), especially those from Furovirus and Bromovirus. The last ORF in RNA2 (p24) is 645 nucleotide long. It is transcribed in a different frame than p61 and p32, and overlaps with the terminal part of the movement protein by 29 nucleotides. Its start codon is located at position 4093 and its stop codon is at position 4737 (UGA). It encodes a protein of 214 amino acids length (SEQ ID NO: 12). This polypeptide has similarity to a glycoprotein precursor (CD47-like protein) from Sheeppox Virus (Tulman, E. R., Afonso, C. L., Lu, Z, Zsak L., Sur, J. H., Sandybaev, N. T., Kerembekova, U. Z., Zaitsev, V. L., Kutish, G. F., Rock, D. L. J. Virol. 76, 6054-61 (2002)). All nucleotide references for RNA2 refer to SEQ. ID. NO: 8.

The sequence of CiLV permitted design of primers to amplify all parts of its genome in overlapping fragments, by RT-PCR (FIG. 1A). Analysis of symptomatic and asymptomatic leaves by RT-PCR (FIG. 1B) showed that only symptomatic leaves contained viral sequences. Northern blots prepared with total RNA extracted from symptomatic and asymptomatic leaves and hybridized to radioactive probes made with DNA fragments from RNA1 and RNA2 showed that only the symptomatic leaves have both 8730 and 4975 bp bands associated to CiL (FIG. 2). Also, RT-PCR made with RNA extracted from viruliferous mites and gene specific primers amplified a 1.7 kb band (FIG. 3). These results associate CiLV genomic sequence to CiL symptoms and the presence of the virus in the vector *B. phoenicis*. Based on these data the new virus is considered to be associated with CiL disease.

SUMMARY OF THE INVENTION

The present invention relates to isolated nucleic acid molecules of and from the genome of a virus that is associated with CiL disease. It is an object of the invention to provide nucleic acid molecules which encode infectious CiLV, and the proteins contained therein. Such nucleic acid molecules are referred to throughout the application as "CiLV nucleic acid molecules".

For purposes of this application, "nucleic acid molecules" refers to RNA, DNA, cDNA or any variant thereof with functions equivalent to RNA, gDNA, and cDNA, such as the synthesis of CiLV polypeptides.

The invention also relates to the use of the CiLV nucleic acid molecules to produce polypeptides, and the resulting polypeptides. "Nucleic acid molecules of the invention" refers to, e.g., CiLV nucleic acid molecules, mutations of CiLV nucleic acid molecules, chimeric nucleic acid molecules and so forth. In one embodiment, polypeptides are produced by cells transformed or transfected with nucleic acid molecules of the invention. In another embodiment, the polypeptide or polypeptides are produced recombinantly from a fragment or portion of the nucleic acid molecules of the invention. In yet another embodiment, the polypeptides are chemically synthesized.

The polypeptides of the invention can serve, e.g., as immunogens to develop diagnostic assays for detecting the presence of CiLV in biological samples, as they provoke antibody production, and the antibodies can then be used in assays.

The invention also relates to the use of CiLV nucleic acid molecules for diagnostic purposes, in which oligonucleotide primers containing from 20 to 100, preferably 30-100, and more preferably, 50-100, and most preferably 30-80 nucleotides presenting from 90 to 100% identity with the CiLV nucleic acid sequences can be used in, e.g., RT-PCR reactions, so that parts of the CiLV nucleic acid molecules can be amplified and detected, e.g., on ordinary agarose gels, thus serving as a diagnostic method for determining the presence of the virus or lack thereof.

The invention also relates to methods of transforming plants, such as monocots or dicots, with constructs containing the CiLV nucleic acid molecules, to produce plants that are resistant to CiLV. Such methods include the introduction of constructs containing at least one CiLV nucleic acid molecule into plant parts, such as scions, rootstock cultivars, and so forth, as well as into *citrus* germplasm and breeding lines. Transformed CiLV-resistant germplasm and breeding lines can be used in conventional breeding programs, to create new cultivars that carry and express the resistance genes.

Accordingly, the invention features (i) isolated and/or purified CiLV nucleic acid molecules that encode polypeptides that have at least 80% sequence identity with the amino acid sequences of SEQ ID NOS: 6, 7, 9, 10, 11 or 12; (ii) the nucleotide sequences set forth at SEQ ID NO: 5 or 8 or sequences complementary to nucleotides, whose complement hybridizes under highly stringent conditions to one of the nucleotide sequences of SEQ ID NOS: 5 or 8.

"Highly stringent conditions", as used herein, refers to parameters with which the art is familiar, such as hybridization in 3.5×SSC, 1×Denhardt's solution, 25 mM sodium phosphate buffer (pH 7.0), 0.5% SDS, and 2 mM EDTA for 18 hours at 65° C., followed by 4 washes of the filter at 65° C. for 20 minutes, in 2×SSC, 0.1% SDS, and a final wash for up to 20 minutes in 0.5×SSC, 0.1% SDS, or 0.3×SSC and 0.1% SDS for greater stringency, and 0.1×SSC, 0.1% SDS for even greater stringency. Other conditions may be substituted, as long as the degree of stringency is equal to that provided herein, using a 0.5×SSC final wash.

The invention also features expression vectors or constructs in which the CiLV nucleic acid molecules are operably linked to one or more expression control sequences or promoters.

The invention further features a transgenic plant, such as one of the genera *Citrus* and *Poncirus*, into which a CiLV nucleic acid molecule has been introduced. Exemplary are *citrus* scions and rootstock cultivars (e.g., from sour orange [*Citrus aurantium*], Rangpur lime [*Citrus limonia*], rough lemon [*Citrus limonia* and *Citrus jambhiri*], mandarin "Cleopatra" [*Citrus reshni], Sunki [Citrus sunki*], Volkamerian lemon [*Citrus volkameriana*], "Caipira" orange [*Citrus sinensis*]) and intrageneric hybrids (e.g., tangelos [*Citrus paradisi*×*Citrus reticulata*], tangors [*Citrus reticulata*×*Citrus sinensis*], citrumelo [*Poncirus trifoliata*×*Citrus maxima*], and citrange [*Citrus sinensis*×*Poncirus trifoliate*]). The plant can be a breeding line. It can also be one from *Fortunella* and *Citrofortunella* species, including calamondin and kumquat. The nucleic acid molecule in the plant includes a selectable marker such as an herbicide resistance gene.

The invention relates to nucleic acids, and the polypeptides they encode, which were identified using sequencing of viral genes from *citrus* plants with or without symptoms of CiL. These sequences come from a newly identified virus which, when it infects a plant, such as a *citrus* plant, causes CiL disease, leading to the death of the plant. Methods of genetic transformation to produce plants that are resistant to CiLV strains are within the scope of the invention. Such methods include the introduction of constructs containing the CiLV sequences into scions and/or rootstocks, so that commercial varieties or any other germplasm useful for breeding programs can be produced and used to create new cultivars resistant to CiLV.

Accordingly, the invention features purified nucleic acid molecules of the genome sequence of CiLV, isolated from *citrus* plants manifesting symptoms of CiL, which, when used in appropriate constructs, have the ability to confer resistance to pathologies caused by CiLV infection in plants infected with CiLV. The isolated nucleic acid molecule can be a portion of a gene, e.g., a nucleic acid molecule whose nucleotide sequence encodes a protein that has at least 80% sequence identity to the amino acid sequence of SEQ ID NOS: 6, 7, 9, 10, 11 or 12. The nucleotide sequences can be that of SEQ ID NOS: 5 or 8 or one that defines polynucleotides whose complement hybridizes under high stringency conditions to the nucleotide sequences of SEQ ID NOS: 5 or 8.

The invention also features expression vectors, isolated recombinant cells, and plants and plant parts containing the nucleic acid molecule of the invention, e.g., one of the nucleic acid molecules described above. The nucleic acid molecule in the vector, cell, seed or plant can be operably linked to one or more expression control sequences or promoters.

In addition, the invention features the isolated proteins encoded by the open reading frames (ORFs) of genes present in the sequence of CiLV. The proteins include amino acid sequences that (a) share at least 80% sequence identity with SEQ ID NOS: 6, 7, 9, 10, 11 or 12; or (b) comprise the amino acid sequences of SEQ ID NOS: 6, 7, 9, 10, 11 or 12. Proteins of the invention can be expressed in bacteria either as "neat" proteins, or as heterologous polypeptides.

The invention also features antibodies raised against the proteins of the invention, e.g., those described above. The antibodies can further include a detectable label.

The invention also features a plant transfected with one of the nucleic acid molecules of the invention, e.g., any purified CiLV sequences. The plant may be of the genera *Citrus* and *Poncirus* (e.g., sweet orange [*Citrus sinensis*], mandarin [*Citrus reticulata*], sour orange [*Citrus aurantium*], Rangpur lime [*Citrus limonia*], rough lemon [*Citrus limonia* and *Citrus jambhiri*], mandarin "Cleopatra" [*Citrus reshni], Sunki [Citrus sunki*], Volkamerian lemon [*Citrus volkameriana*], "Caipira" orange [*Citrus sinensis*]) and intrageneric hybrids (e.g., tangelos [*Citrus paradisi*×*Citrus reticulata*], tangors [*Citrus reticulata*×*Citrus sinensis*], citrumelo [*Poncirus trifoliata*×*Citrus maxima*], and citrange [*Citrus sinensis*×*Poncirus trifoliate*]). The plant can be a breeding line. It can also be one from *Fortunella* and *Citrofortunella* species, including calamondin and kumquat.

The invention features a method of producing a disease resistant plant by introducing constructs containing purified nucleic acid molecules under the control of a suitable plant promoter, into the plant, transforming the plant with *Agrobacterium* strains or microprojectile bombardment.

All technical terms used herein are terms commonly used in biochemistry, molecular biology, phytopathology and agriculture, and will be understood by one of ordinary skill in the art to which this invention belongs. Those technical terms can be found in, e.g., Molecular Cloning: A Laboratory Manual, 3rd ed., vol. 1-3, ed. Sambrook and Russel, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, $5^{th}$ ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methods involving plant biology techniques are described herein and are described in detail in methodology treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described, e.g., in Innis et al., PCR Protocols: A Guide to Methods and Applications, Academic Press, San Diego, 1990 and in Dieffenbach and Dveksler, PCR Primer: A Laboratory Manual, $2^{nd}$ ed., Cold Spring Harbor Laboratory Press, Cold Spring Harbor, N.Y., 2003. PCR-primer pairs can be derived from known sequences by known techniques such as using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Caruthers (1981) Tetra. Letts. 22:1859-1862 and Matteucci and Caruthers (1981) J. Am. Chem. Soc. 103:3185.

BRIEF DESCRIPTION OF THE DRAWINGS

The invention can be more readily understood by reference to the accompanying drawings, wherein:

FIG. 1A shows the localization of the primers used in RT-PCR along the two RNAs of the CiLV genome. FIG. 1B shows the results of diagnostic RT-PCR for CiL performed on total RNA isolated from symptomatic leaves collected from 4 different regions in the State of São Paulo, Brazil, and asymptomatic leaves from Piracicaba, State of São Paulo, Brazil.

FIG. 2 shows the Northern blot for RNA1 and RNA2 from symptomatic and asymptomatic leaves.

DETAILED DESCRIPTION OF PREFERRED EMBODIMENTS

Figure 1A:
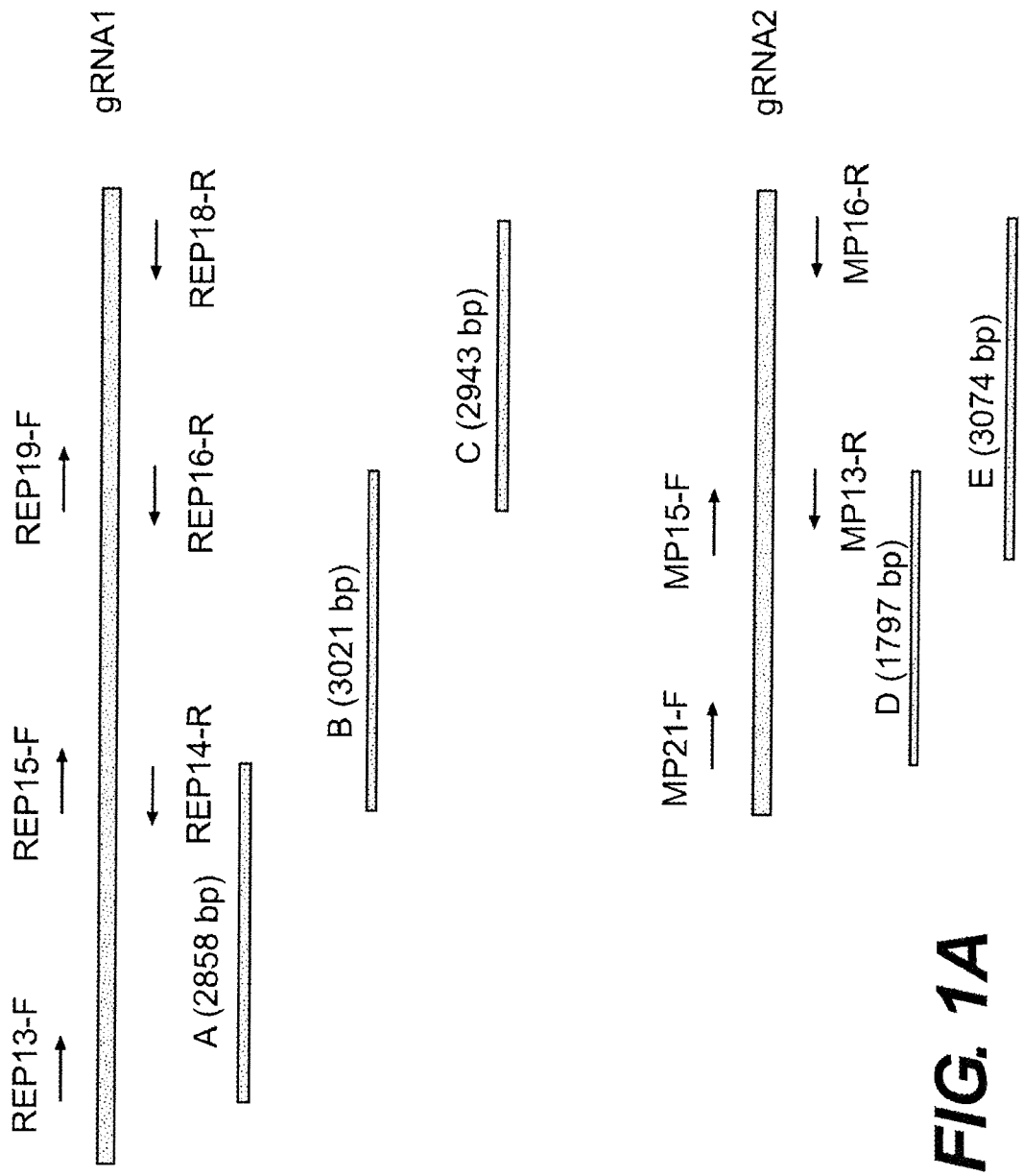
Figure 3:
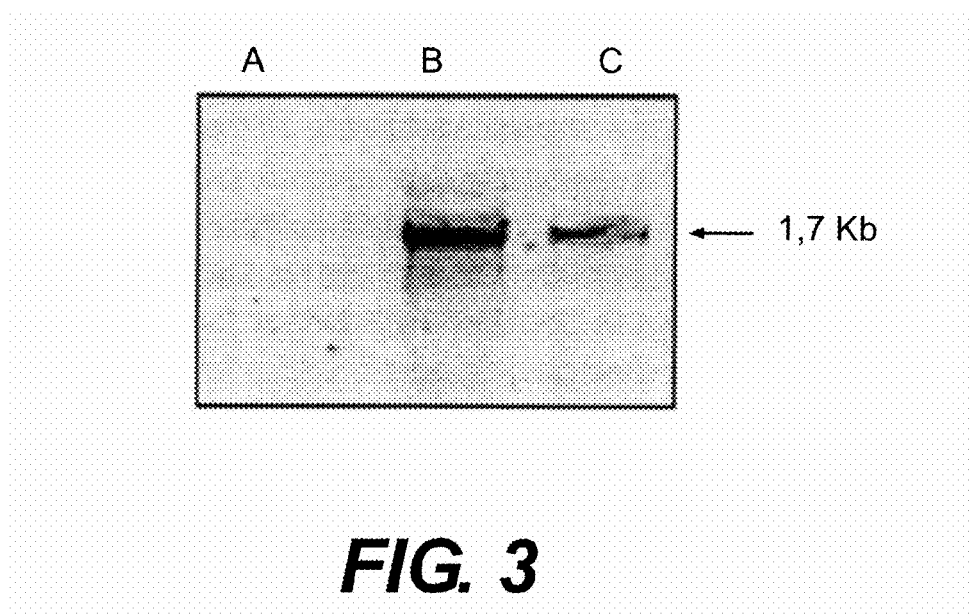
FIG. 3 shows the amplification of CiLV sequence by RT-PCR from total RNA extracted from viruliferous mites and leaves.

Nucleic acid molecules from the genome of a virus that causes *Citrus* Leprosis (CiL) have been cloned and sequenced. Such nucleic acid molecules are referred to throughout the application as "CiLV nucleic acid molecules". Polypeptides encoded by CiLV nucleic acid molecules have been analyzed using software programs including BLAST, and have been shown to encode, inter alia, a Replicase involved in virus replication and a Movement Protein involved in the translocation of the virus throughout the plant.

The molecular cloning of CiLV nucleic acid molecules provides the means to develop diagnostic methods to detect the presence of CiLV in biological samples, including, but not being limited to, tissues, cells and organs of plants, such as plants of the genus *Citrus*. The molecular cloning of CiLV nucleic acid molecules also provides the means to create CiL-resistant plants, such as those of the genus *Citrus* through genetic transformation. Genetic transformation of plants can be secured via *Agrobacterium* transformation methods. Such methods include cloning constructs containing CiLV nucleic acid molecules operably ligated to promoter and enhancer regions, initiation and termination sequences. These constructs can also contain genes for selectable markers, such as herbicide resistance. These constructs may be cloned in the Ti plasmid of *Agrobacterium*. Plasmid vector-containing constructs are used to transform commonly used *Agrobacterium* strains, which are subsequently used to transform plants, such as those of the genus *Citrus*. Plasmid vector-containing constructs may be also introduced into plants by microprojectile bombardment. The constructs containing the CiLV nucleic acid molecules are useful for creating CiL resistant plants such as all common types of *citrus* fruits, including, but not limited to, sweet oranges, grapefruit, mandarins, tangerines, pummelos, lemons, limes, citrons, bergamots, limequats, meyer lemons, silver limes, key limes, kaffir limes, lavender gems, blood oranges, satsumas, oroblancos, melogolds, intrageneric hybrids such as tangelos and tangors, and *citrus*-type fruit such as calamondins and kumquats (*Fortunella* spp.). For example, resistance gene molecules can be introduced into commercially utilized rootstock cultivars, including, but not being limited to, Rangpur lime, sour orange, rough lemon, various mandarins, and *citrus* intrageneric and intergeneric hybrids. CiL resistant *citrus* plants, composed of genetic modified scions and rootstocks, can then be used by *citrus* growers to counter CiL disease, and to avoid decreasing productivity and/or tree death and replanting costs.

Methods involving conventional molecular biology techniques can be found in the following references: Molecular Cloning: A Laboratory Manual, 3rd ed., vol. 1-3, ed. Sambrook and Russel, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, $5^{th}$ ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methods involving plant biology techniques are described herein and are described in detail in methodology treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described, e.g., in Innis et al., PCR Protocols: A Guide to Methods and Applications, Academic Press, San Diego, 1990 and in Dieffenbach and Dveksler, PCR Primer: A Laboratory Manual, $2^{nd}$ ed., Cold Spring Harbor Laboratory Press, Cold Spring Harbor, N.Y., 2003. PCR-primer pairs can be derived from known sequences by known techniques such as using computer programs intended for that purpose (e.g., Primer, Version 0.5, 1991, Whitehead Institute for Biomedical Research, Cambridge, Mass.). Methods for chemical synthesis of nucleic acids are discussed, for example, in Beaucage and Caruthers (1981) Tetra. Letts. 22:1859-1862 and Matteucci and Caruthers (1981) J. Am. Chem. Soc. 103:3185. Chemical synthesis of nucleic acids can be performed, for example, on commercial automated oligonucleotide synthesizers.

The invention provides purified nucleic acid molecules (polynucleotides) that encode polypeptides having an amino acid sequence selected from the group consisting of SEQ ID NOS: 6, 7, 9, 10, 11 and 12.

The CiLV nucleic acid molecules of the present invention can be obtained from CiLV infected plants. The molecules of the present invention may be in the form of RNA or DNA, preferably in the form of cDNA. The cDNA may be double- or single-stranded, and, if single-stranded, may be the coding (sense) strand or noncoding (anti-sense) strand. The sequence may be identical to a nucleotide sequence consisting of SEQ ID NOS: 5 or 8. It may also be a different coding sequence which, as a result of the redundancy or degeneracy of the genetic code, encodes the same polypeptide as the sequences of SEQ ID NOS: 5 or 8. Other nucleic acid molecules within the invention are variants of CiLV nucleic acid molecules such as those that encode fragments, analogs and derivatives of native CiLV nucleic acid molecules. Such variants may be, e.g., naturally occurring polymorphic variants of native CiLV nucleic acid molecules, or a non-naturally occurring variant of native CiLV nucleic acid molecules. For example, the nucleotide sequence of such variants can feature a deletion, addition, or substitution of one or more nucleotides of native CiLV nucleic acid molecules.

Naturally occurring variants of native CiLV nucleic acid molecules within the invention are nucleic acids isolated from CiLV infected plants that have at least 65% sequence identity with native CiLV nucleic acid molecules, and encode polypeptides having at least one functional activity in common with native CiLV nucleic acid molecules encoding proteins.

Shorter oligonucleotides (e.g., those of 6-200, preferably 12-150, more preferably 30-125, and even more preferably 50-100 base pairs in length) that match perfectly to the CiLV nucleic acid molecules or hybridize with CiLV nucleic acid molecules at stringent conditions as defined herein can be used as probes, primers, or antisense molecules.

Longer polynucleotides (e.g., those of 300 to 800 base pairs) that encode or hybridize with CiLV nucleic acid molecules can be used in place of a native CiLV nucleic acid molecule in applications where it is desired to modulate the functional activity of a native CiLV nucleic acid molecule.

Nucleic acids molecules that hybridize under stringent conditions as defined herein to a nucleic acid selected from the group consisting of SEQ ID NOS: 5 and 8 or to the complement of a sequence selected from the group consisting of SEQ ID NOS: 5 and 8 are also within the invention. For example, such nucleic acids can be those that hybridize to a sequence selected from the group consisting of SEQ ID NOS: 5 and 8 or to the complement of a sequence selected from the group consisting of SEQ ID NOS: 5 and 8 under low stringency conditions, moderate stringency conditions, or high stringency conditions are within the invention. Preferred nucleic acids molecules are those having a nucleotide sequence that is the complement of all or a portion of a sequence selected from the group consisting of SEQ ID NOS: 5 and 8. Other variants of CiLV nucleic acid molecules within the invention are polynucleotides that share at least 65% sequence identity to a sequence selected from the group consisting of SEQ ID NOS: 5 and 8 or to the complement of a sequence selected from the group consisting of SEQ ID NOS: 5 and 8.

CiLV nucleic acid molecules encoding polypeptides are also within the invention. Such polypeptides can be made by preparing a construct (e.g., an expression vector) that expresses CiLV nucleic acid molecules encoding polypeptides, when introduced into a suitable host. Variant CiLV nucleic acid molecules-encoding polypeptides can be produced by those skilled in molecular biology procedures using standard nucleic acid mutagenesis techniques or chemical synthesis.

Another aspect of the invention relates to the use of purified antisense nucleic acid molecules to inhibit expression of CiLV nucleic acid molecules. Antisense nucleic acid molecules within the invention are those that specifically hybridize under cellular conditions to cellular mRNA and/or genomic RNA of CiLV in a manner that inhibits expression of the genes encoded by the CiLV genome.

The antisense nucleic acid molecules should be delivered into cells that express CiLV genes. For instance, constructs expressing antisense molecules under the control of a strong promoter can be introduced into *citrus* plants by genetic transformation using *Agrobacterium* or microprojectile bombardment (Ghorbel et al. Tree Physiology. 20. 1183-1189 (2000); Bespalhok et al., Crop Breed. Appl. Biotech. 1. 27-34 (2001); Bespalhok et al., Braz. Arch. Biol. Technol. 46. 1. 1-6 (2003); Molinari et al., Scientia Horticulturae. 99.3-4. 379-385 (2004); Jia-Long et al., Plant Science. 113. 2. 175-183 (1996)).

The expression of CiLV nucleic acid molecules can be modulated by RNA interference (RNAi) (Lee et al. Nature Biotech. 19. 500-505 (2002); Voinnet, O. Trends Genet. 17. 449-459 (2001)) by which a construct driving the synthesis of sequence-specific double-stranded RNA (dsRNA) is introduced into an organism or cell in order to silence the targeted gene (Hannon, Nature. 418. 244-251 (2002)). Selected sequences corresponding to CiLV nucleic acid molecules can be used to create, after expression, a sequence-specific dsRNA that can interfere with accumulation of endogenous RNA encoded by the CiLV nucleic acid molecules.

The present invention is further illustrated by the following specific examples. The examples are provided for illustration only and are not to be construed as limiting the scope or content of the invention in any way.

Example 1

This example describes the identification and cloning of nucleic acid molecules from CiLV by RT-PCR. Total RNA was extracted from symptomatic and asymptomatic leaves. First strand cDNA was synthesized using 4 µg of total RNA as template, 250 ηg of oligonucleotides, and was denatured at 65° C. for 5 minutes. The solution was then incubated on ice while adding 1 µl of 10 mM dNTP mix and 3 µl of First Strand buffer (250 mM Tris-HCl, pH 8.3, 375 mM KCl, 15 mM $MgCl_2$) to the tube. The mixture was incubated at room temperature for 2 min, 1 µl (200 U) of reverse transcriptase was added and the solution was further incubated at room temperature for 10 min. followed by 60 min. at 42° C. For PCR, 2 µl of the first strand cDNA was used as template, 0.125 mM each dNTP, 2 mM $MgCl_2$, 1× reaction buffer (20 Mm Tris-HCl, pH 8.4, 50 mM KCl), 1 U of Taq polymerase and 0.4 µM of each of primer pair: REP13 5' ACAGACTACGTGAAAATATACC 3' (SEQ ID NO. 13) and REP14 5' CGTGAAACTCCGAATCCATT 3' (SEQ ID NO 14); REP15 5' GGAAATTGCTTCCTCACTTG 3' (SEQ ID NO 15) and REP16 5' GGTGTTGTGGTACCACCACC 3' (SEQ ID NO 16); REP19 5' GTACCGCACTTGAGCCTATC 3' (SEQ ID NO 17) and REP18 5' AACCTCGCCCAGCTGACAAC 3' (SEQ ID NO 18); MP21 5' GGTTGCTTTACGTTCGAGTGTGA 3' (SEQ ID NO 19) and MP13 5' CGTTGTGGAGACCCAGAGCA 3' (SEQ ID NO 20); MP15 5' GGTAGTGATATCATGTCATGTG 3' (SEQ ID NO 21) and MP16 5' GGTACACCACCAGCTAGAAG 3' (SEQ ID NO 22). *Citrus* chalcone synthase primers were used as internal controls. The reaction was heated for 5 min. at 94° C. and subjected to 30 amplification cycles (30 s at 94° C., 30 s at 55° C., 1 min at 72° C.). DNA fragments were separated in a 1% agarose gel, stained with 100 ng/ml ethidium bromide and analyzed under UV light (FIG. 1B). The bands generated by RT-PCR were cloned in pGEM-T and sequenced using an ABI 3700 sequencer. The BLASTX and BLASTN against NR databases showed sequence similarity to the Movement protein of *Sorghum* Chlorotic Spot Virus (BAA94804) and the replicase protein of Barley Strip Mosaic Protein (NP_604474).

Example 2

In this experiment Northern blotting was carried out on RNA samples extracted from symptomatic and asymptomatic leaves. DNA fragments from the movement protein and replicase partial genes CiLV were used as probes. FIG. 2 shows the band pattern in symptomatic plants and positive controls with both probes, while no bands were identified in the asymptomatic material with both probes.

Total RNA from bark tissue of symptomatic and asymptomatic plants was extracted using the Trizol Reagent (Invitrogen) according to the manufacturer's protocol. Ten micrograms of total RNA from each sample were separated by denaturing electrophoresis on a 1% agarose gel containing 1×MOPS and 0.6M formaldehyde, according to Sambrook and Russell (2001), supra. The gel was subsequently transferred to a Hybond-N+ nylon membrane by capillary transfer in 10×SSC (1×SSC is 0.15M NaCl; 0.015M sodium citrate) for 16 hours. The membrane was baked at 80° C. for 2 hours, prehybridized in hybridization buffer for 2 hours at 65° C., followed by hybridization in a fresh aliquot of solution containing 20 ng/ml of probe ($2 \times 10^7$ cpm/ml) for 16 hours at 65° C. The probes consisted of a 339 bp fragment of the CiLV Movement protein and 402 bp fragment from the Replicase gene. The probe was radioactively labeled by random-priming with [α-32P]dCTP (6000 ci/mmol) using commercially available products. After hybridization, the membrane was washed at room temperature in 2×SSC, 0.05% SDS for 4×10 min, and then twice at 55° C. for 20 min each in 0.1×SSC; 0.1% SDS. The blot was exposed for 1 hour and analyzed by phosphoimaging.

Example 3

This example describes the identification and cloning of nucleic acid molecules from CiLV-C by RT-PCR from viruliferous mites. First strand cDNA was synthesized using 4 µg of total RNA as template, 250 ηg of oligonucleotides and denatured at 65° C. for 5 minutes. The solution was then incubated on ice while adding 1 μl of 10 mM dNTP mix and 3 μl of First Strand buffer (250 mM Tris-HCl, pH 8.3, 375 mM KCl, 15 mM MgCl$_2$) to the tube. The mixture was incubated at room temperature for 2 min, 1 μl (200 U) of reverse transcriptase was added and the solution was further incubated at room temperature for 10 min. followed by 60 min. at 42° C. For PCR, 2 μl of the first strand cDNA was used as template, 0.125 mM each dNTP, 2 mM MgCl$_2$, 1× reaction buffer (20 mM Tris-HCl, pH 8.4, 50 mM KCl), 1 U of Taq polymerase and 0.4 μM primers: MP21 5' GGTTGCTTTACGTTCGAGTGTGA 3' (SEQ ID NO 19) and MP13 5' CGTTGTGGAGACCCAGAGCA 3' (SEQ ID NO 20). The reaction was heated for 5 min. at 94° C. and subjected to 30 amplification cycles (30 s at 94° C., 30 s at 55° C., 1 min at 72° C.). DNA fragments were separated in a 1 agarose gel, stained with 100 ng/ml ethidium bromide and analyzed under UV light (FIG. 1B). The bands generated by RT-PCR were cloned in pGEM-T and sequenced using an ABI 3700 sequencer. The BLASTX and BLASTN against NR databases showed sequence similarity to the Movement protein of *Sorghum* Chlorotic Spot Virus (BAA94804).

The invention claimed is:

1. A recombinant expression vector comprising an isolated cDNA molecule which encodes a full length citrus leprosis virus protein, the complementary sequence of which hybridizes, under stringent conditions, over the full length sequence set forth in SEQ ID NO: 5, operably linked to a heterologous promoter, wherein the isolated cDNA molecule encodes a protein having the amino acid sequence set forth in SEQ ID NO: 7.

2. The recombinant expression vector of claim 1, wherein the isolated cDNA molecule comprises the isolated nucleic acid molecule, and at least one other nucleic acid molecule.

3. An isolated, recombinant cell, transformed or transfected with the recombinant expression vector of claim 1.

4. The isolated, recombinant cell of claim 3, wherein said cell is a eukaryotic cell.

5. The isolated, recombinant cell of claim 4, wherein said eukaryotic cell is a plant cell.

6. The isolated recombinant cell of claim 5, wherein said plant cell is a *Citrus* cell or *Poncirus* cell.

7. The isolated recombinant cell of claim 5, wherein said plant cell is a dicot cell.

8. A transgenic plant or plant part comprising the recombinant expression vector of claim 1.

9. The transgenic plant of claim 8, wherein said plant is selected from a *Citrus* plant, *Poncirus* plant, or other plant used in a citrus breeding program.

10. The transgenic plant of claim 8, wherein said plant is a dicot.

11. The transgenic plant part of claim 8, wherein said plant part is a leaf, flower, stem, root, tuber, fruit, pollen, or seed.

12. The transgenic plant of claim 10, wherein said plant is a citrus plant.

13. A method for determining if a plant is susceptible to citrus leprosis, comprising contacting a sample of said plant with the recombinant expression vector, and determining hybridization of said recombinant expression vector to a target as a determination of susceptibility to citrus leprosis.

14. The method of claim 13, comprising polymerase chain reaction.

15. A recombinant expression vector comprising an isolated cDNA molecule encoding a citrus leprosis virus protein, wherein said nucleic acid molecule has the full length sequence set forth in SEQ ID NO: 5, operably linked to a heterologous promoter.

16. A recombinant expression vector comprising an isolated cDNA molecule which encodes a citrus leprosis virus protein, having the amino acid sequence recited in SEQ ID NO: 7, operably linked to a heterologous promoter.

17. An isolated, recombinant cell comprising a recombinant expression vector of claim 15.

18. The isolated, recombinant cell of claim 17, wherein said cell is a plant cell.

19. The isolated, recombinant cell of claim 17, wherein said cell is a plant cell is from a *Citrus* plant, *Poncirus* plant, or other plant used in a citrus breeding program.

20. The recombinant expression vector of claim 1, wherein the cDNA molecule encodes a protein having the amino acid sequence set forth in SEQ ID NO: 6.

* * * * *

```
                        SEQUENCE LISTING

<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcgtattggc gttggatttc tgac                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgtataccaa gccgcctgtg aact                                            24

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatacgggac gcataaca                                                   18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttctggctca acatctgg                                                   18

<210> SEQ ID NO 5
<211> LENGTH: 8730
<212> TYPE: DNA
<213> ORGANISM: Citrus Leprosis virus

<400> SEQUENCE: 5
gataaaactg tcaagtgata taccacatta cttggcaaaa ttttctgttg tgcttacaga     60
```

```
ctacgtgaaa tataccaaat tttaaccagt gtagagctat accaaagatg tctacacata    120
gcaccgttga aactctggac gttaacagag ttagggagct tctcagaagc catcgtgagg    180
cttcatcaca ttgtgatgaa cctaggttca cggcgacaca taccaaaggt cgggtcgtgg    240
cctcatctga gaagcccct gtatccttta caatcgcaaa tgggcagatc gttagcgaca     300
gtgaggttat tacttccact gaagctaagg ctgcggcgat tttatctgtg atttcctcct    360
acccaaagga gattcgtgag cagctcaatg ggagaattga acgtggcttc accgacaatc    420
cagatgtcga tgaggccgcg cgttgtatcc attctgctcg tttacacaat atcacaacga    480
ctgctcttcg taagaaaccc cttcttgtgc atgagaatgt ctccaatgat atggaaagat    540
tcttaaacga gaagtttttg ggttataaga ttaggctcac ctgtagtaaa aatgtggcac    600
ataacaacgc tgctgcgttg cgtcgtgtgc tacgttttta catgcgtgat aaagtgggtt    660
acaggaaaga cgacgacata cccgaggggt atcacgtcaa gaacaaagac gttggcgcat    720
cggggatgga tgttatcgcc gatgaattga ccgatgttca ctgctgtaca ccagacttag    780
actttcgtga ccacataagg ctagagaggc tgaagaagta tatctactct catgtatgtc    840
caacgtctaa ggatcacggt attatatgcg agggctttcg tgaaggatcc acaaaataca    900
gatgtgaaaa tataggtcag cagtgttata ttaaggcacc aacgttgact tttgtccata    960
gtgcctatga tattaccgct gctggtattg tcgactgtat gattgcagct aatgctcatc   1020
atgctatcat gtgcctacat tttccatctg ctatactttc tggttcaaca tctggtaaag   1080
atgatctact gcaatacaaa tgggatattg tagtggagga tggcattaag tattataaac   1140 aaaaatttt gaacgataca caggcatcat atgttcatag gttggatgtg tatctcgata   1200 agttttttgac taaagtggtc cttgggagcg ataagcgatt ctacatgttc gagattactg   1260
agatgtttgg ttctgttgcc ataatcgaag tatttcgccg tgagaaggat tttattgctg   1320 gttccaaaact cacttttaat atacccagga cagagcatcc taacacagtc acaattcaca   1380
cttgggaata tgtgactggt tatgagagtc tgttcaaggg ccgtaatgga cttaagtctg   1440
gtgttatgcg tcccgtatct attgaagtcc ctgaggaatt tttcctcagt gttttcaagt   1500
atggtatgac cgttgactcc aacaagttcg tttacgatgg gttgcttaaa agtggtgttg   1560
ggattgctgc gaggcggaat attggtggta ccaccatggt cgatccgtct tctcctattc   1620
ctgtacgtaa gttgcaaacc tttattgtta ctatgtatat gttgctttac caggagaagt   1680
gggaagcgac acagggtttg gtaactatga agatgttagc tgatcagtac aggactagga   1740
gctccaaaaa tggtattgta cggtttctta caaacgtctt ttctcctgac aaagtcggtg   1800
agacgcaaca ccccttcatcc acttatgatt taggtaagct gggtttctcc cactcggagg   1860
acaataagtt cgtttgcgat aggaatctga ataccgagga gaggtctcgt ctgagtcagt   1920
tcgagaggct ggttcaatgg ttccgtgagt tttcacgtgt ccatagaaag tgccctattg   1980
tcgtccatga ctctacacat atgcttgagt atgttctgga catcccagat atggttgtgc   2040
agaacataaa gagcctgcgt gacgatctta cccttagtaa tttatgcgat catgattttg   2100
acgcatactt accgagtcac attgaggtta tgatgcgaa gtgcaccaaa gacctcacag    2160
tgatccaggt gcctggcgat ggtaattgtt tgtactactg tttcgtcaag gcgtgcctgt   2220
ataggggtat atcagtctgc gatttgaaaa gtaggctgag agactctcca tacttttttg   2280g aggtcgcgaa acttgctcgc gactctggcg aagatgagtt ccttgactct ttggaacgtg   2340
atggtgttta cggtaataag tttacgctga ttccttatcag caaaacttt aacgttaata   2400 tttgcgttca ccttaaaggt ggtcgcgaat tgattacaca cttcatctct aacaaaggtt   2460
```

```
cgaggttcat tcatcttcaa ttagagcata gccattatag cttgcttgta ccatgtatta    2520
aagctggtct tattgatgag catgttttat gtcatggtgc actgagcatg gtagtgccaa    2580
ctgcgcatga ttataggcgt cttgtggacc tttataagat ttatactaga gatggtacta    2640
ttgcgtcata ttttaatata tttaacaatt cttataaggg cccgttctta aatgtctatg    2700
agctaggctt tatggaaatt gcttcctcac ttgagattcc ctcaagtagt gggaacaaat    2760
tccttattac cgatgtgtgg ttacatcatt gcattaaggc tttgagagtt ttggatccgc    2820
attctaatgt tatagtttta cggagttcca atacttctag gatccctgat agatatggcg    2880
tgtgtgactt tacaatggat tcggagtttc acgaagaatc cttttgcttg tcaaccacgc    2940
tatccgacgt acttaatttg ggaatttatt ctcaatgtat ggtagtcttt tctgatctct    3000
cacgggttcc tttaaagcct tttgctcccg gattcaggac gcgcacttct gttgctgaac    3060
gttccaacaa gattttgctg gcttggtcag cgttgtcttc aggtgggact gcagttttta    3120
gggtatttcg tcctgaagaa gttccagaat ccttgaatat gctaaccacg ctatttgagg    3180
atattaggtt cttcaaacca aaggctatct cgacatcaat tgttgatgga tatctacttt    3240
gtagtggtaa acgctctcac cctggtagtg agttctcaat cacgagcgag gtgcgtaacc    3300
atttttatac ggttaatgtc gagaactttt ataaacaaac cttagaagag tctgaagtgt    3360
ccaactatgt taaggacttg tgcggtttgt atgctggtgg tggattcgtt aaaccaacac    3420
gtaagcattc gtataaccgc tcgtttgtct tggacagatc tcttattcta tcaaaactta    3480
tggaattctc aagcagcgtc tcgtttgggc tgtttggtag gaagttctcg acttacaaat    3540
tacatgtcgg ttgtgatact aaactaaagt tttgtaatag gagtattgag gaaatacttg    3600
actcgcaatg tttacattgt aagtactcta agtacgactt caattctttg agatcggtgt    3660
cggacttggc ttcgtttgct acgcgtgaac gtgctgtggt tgtggagaca tttgatgatt    3720
gtggcgatta tgtttcgatc atatcatttt tccacaagct atattctatg tgttttaagg    3780
accttcgcgt tgttagtgat tgtttcctga ataatgtcgt acttaagagc ttttttagctt    3840 acgcgcgatg ctattcagat gttgagatat ctttatgcca acttaaggga aggttgctag    3900
ttgacatcac ttgtcgctct agttggtaca atggatgtga atttggtgac ttcgagctgg    3960
tttcgtgcaa taggcatgac tatgacacag cttttgttga ggtgttaatt cagcatgcaa    4020
tgcataacca gcgttacaac aatgagacaa tcgttataaa ttcgagggct gatgccattc    4080
gcgcgggtct ctcagtgcgt aagttcaaac catgcggtga tgtacttgac gatttgaata    4140
agtctgttaa gtacaagcct aagtttgtca cttacaacac tgaaagtctt gtgaacagta    4200
ttaaggccat cgttggtgtt ggtgacgaaa ctaccaagga gcctaccgac aattcggttg    4260
ttgaaaagcc ggtagtagtc tttgagaagg ttgattcacc taacctcgac gatcgtatta    4320
aagctgtcta cgagtacagg tcgtacatgg gtagggagct atctcatagt aacgacgtac    4380
tcgaaaagac cgtctccaac ttgttgcggt ttacggagac acgtgatcct aagaggctta    4440
atgagatgta ctttccgaat tcatctttct tgtctgatga gatgaagctt aaagacagtg    4500
tcggaataat cacttgcaat ggtaagattc ttaagaattc tgaacccatt gtgcaatttg    4560
acgatatctc tgctgtttat gatatagtca atggttctgt ggttgataag tctgactact    4620
tcaagatgca tagaggtaag accaccaaac aagtcggtgg ttttgcgatt tatactagcc    4680
ttgttgcaca taatcaggtt gaaagtatct gaaggcagt agactgcgtt tatgcctctg    4740
aaaagattaa tgaccttagt gcgatttcga ttgattgggt acaagctgtg gctggtgctg    4800
```

```
ggaagacgac tttgttagtc gagacctttt taattactga cttagtcgta tgcccaaccg   4860
ttgaaaatcg cgattctatt cgtttacgca ttaagcgtcg ttatcctgat ttggatccga   4920
aagaagtcga ttgccgtgtc agaaccatca acgggtatct tgttgacttc tctactaagt   4980
tggcaaaggt cactcttaat gagaacacta ggttgcttgt tgatgaagct attatgtatc   5040
atgctggttg tctgtttgtc ctatgcatga tttataatat taggcgtatg ttctgcgttg   5100
gcgataagaa gcagatacct tttgtttcta ggatcgactt taagttgaat tatgagaaat   5160
tgtgtgattt tgtcaacact gaggcgagac ccctggctag gactttccgt agtcctccag   5220
atgttaccta ccgtatgcag caaatttacg gtaagtcact taaaggcctg accatacagt   5280
gtttgagcaa gaatcaggac acttctccaa gcgtctctaa gcttgtcatc acaaagaatt   5340
ataggtttgg acagaatttt atacgcgaag tctttgaaaa agataaaatt gacttcgacg   5400
gtaagaatct gcgtatccta ttttccttc gtgaagacat gcttagcttt tatggtaatg   5460
gtggtatgat ctttacagat tgctgtagta ctatacacca gtttcagggt agtgacgctg   5520
aatatgttgt tgtcatgcgc ctgacatatg ctgagaagtc tatttttatg gatgaaaggc   5580
aatgtcttgt cgcattgact aggcatacta agcgtatggt ctacgtaagt gttaatgaag   5640
gtactgatgt actcacacgg tggataaata tgccagtagt tgagtccatg ttagtaccgc   5700
acttgagcct atctggtggt ggtaccacaa caccgtcgag atatgtcacg tatcgctcta   5760
ttccatctgt tgaccttatg aagggagata agtgcgttcg cgttggttat cacccacgaa   5820
gtgacattat tttggataag cgtgacacct tgactgctgt cttgaataag attgccgacg   5880
cacgacctaa gggtaacttg gtggtgtcgt cggcagtctt agacaagttc aaccagcaaa   5940
gattgaaacc cttgcttaaa tccatcgtcg gccactcaaa catatttgc gccggcgtga   6000 acagcaatat aaacagcaca gtttttgagg tcatgcagct taacgcggtt gatcatgtac   6060
ctaaccactt catagatcct atctttgatg acgatgttgt aaggtctgca gatattggtt   6120
acaaacccta taggcaacat gacaaccatg atcctgtatt gtcggactat ggatttgatg   6180
ataagtttgc ggtcatccaa aatttttat gcacaacgtt tcctaatagt tgttacgtac   6240
cgaattatat ggatgcctgg ataacttata atcttgactt agatttagct attgatgata   6300
ttgttatcaa tgttatcaag tttgctacca tcgataggac ctatgactgc atgattccta   6360
gacttagctt ctgctcacct gtagttagaa aggcctgctt ggtggagagt ttgattgctg   6420
tgcaaaagcg taatcgcaat gttcctcaat tatcatctga ggtttcgcca tatgttatgg   6480
cggatcagtt attcgactcc ctacgcagct tacttgacga acgctactac caggaggtac   6540
attatgggcc tgctgagttg gctgcgtggt tgaatgacca gaagggtagt gtagttgatg   6600
aggtaattgg agaatattgc atttactcta ctgctgttga gaggtaccag cttatcacca   6660
agaatagtcc taaacctact ctttctgatg aggcctacat ggagttcgct gctcctcagg   6720
tggtacttca ccagacgaag gatattaatg ctgtgttttg tgtaatctgg aggggtatta   6780
agacggtcgt ccagagtatg ctacgacacc acaataatat ctttatgttt gcggatatgg   6840
atcctgactc atttgcggat ctactaactg agaaggttag tacgaaggtt caggagactt   6900
tcgattctct tgaaatcgac attaagaagt acgacaagtc acaggatttg aaggtacttc   6960 ttccttgaatg caagctcctg cgatactttg tgtgtctcgga agagcttgtt attatttggt   7020
tcaagtcaca tgttgagtcc atcgttaaag ataggagatc aggattaaag tttaaggtgc   7080
aggtgcaacg ccgttctggt gatggtggta catttatcgg taacacactt ttcctcatag   7140
tgttgtgtgc acgtaacttt gatctgcgca agctgaagtt agcggtcttt tccggtgatg   7200
```

```
attcacttttt agttggtgag aaacgtgacc tccagtgtga tagtcagaat ttttctgatt    7260
tgttcaacct ggatgtgaaa ttctttccta actttaagta ttatcacttt tgttcaaaat    7320
ttttgatagc tgttgaggat cgttggtact ttatccctga tccagtgaag ttgtgcattc    7380
gtttggcgcg acttgacttg gttaattggg gtcatattga agagtaccgt atatcattga    7440
aagatacaac gaagtattat tgtgatgaca gtattgttcg tgagctctct aaggcagttt    7500
gcgatagata tccggtggct gttgaccctg ctgaggtctt tagagtcgta tgctctatag    7560
tctcaagtaa ggacgagttt aggttgctct tgaggaacc gctcgcttgt ctccctgagg     7620
gtaatttgct tcctgtcatt aattaaagta atactgactt ttatgatact attattgata    7680
ttttaccgcg aatttgtatt ttgtcattat gagtatcgta actttcactt tgactgaccc    7740
ttcctctgct tgattgctg agattatgca ggccattgag cggcacaatg tgtctgttcc     7800
tgaaggtctg cgtgatatta gcaagcctac taagaagaag cagcagtcgc aacctcaaca    7860
actgtcacga gcgtcagcgc gccctcagca actgcaaccc ggtcctagtg gttatcaggc    7920
caagaaacct gctaagcaga aggccgaggt tgtaaagccg aagcagaagc agctcgctcc    7980
acccataaat aagaaagcgg cgaaagccaa actttatggg ttggagcaac actgcccaaa    8040
gtatgccgag gcgaaggggc tgcagaagca gatagggatg acatattata agatatccga    8100
gccctatgca ttacctgatt ttaaggtaat ggaagcttct gaggacctag ttgccgtcag    8160
tgagaaggac ccaatgggta gctttgagaa gcgcttatat agtatgggct tcccgaagcg    8220
acccataaag aacgttgtcc cggtattcga gttcagtgat cactacattg tggtgttctt    8280
ccctggctcg aatgctgaga tagttaagaa cgttcctaag gactccgttt ctgattatgc    8340
agaggcacaa cttgctgcgc tccttgctgc tagacagcag attaatcaaa tccacgaact    8400
gggcgacatc ttacctacca attatctgaa tgttttagat agtggtacac aagatgtcgt    8460
cgtgtctgat gaggaggatg actccgactc agcgcagtag gtcggtggat taatgatggg    8520
ggttttcttg cggttctttc cctcattcta ttttgaatcg ctaatctctg gtactttttg    8580
tgctggagat tatctgaact tacgttcggt ccggtcgttg tcagctgggc gaggtttgaa    8640
ttcctcaatt ttgattaatt tctagtctct tccagctggt ggcgtaccac cttttctttt    8700
taatttttct tttcttttgt ctttatgaca                                     8730
```

<210> SEQ ID NO 6
<211> LENGTH: 2512
<212> TYPE: PRT
<213> ORGANISM: Citrus Leprosis virus

<400> SEQUENCE: 6

Met Ser Thr His Ser Thr Val Glu Thr Leu Asp Val Asn Arg Val Arg
1               5                   10                  15

Glu Leu Leu Arg Ser His Arg Glu Ala Ser Ser His Cys Asp Glu Pro
                20                  25                  30

Arg Phe Thr Ala Thr His Thr Lys Gly Arg Val Val Ala Ser Ser Glu
            35                  40                  45

Lys Pro Pro Val Ser Phe Thr Ile Ala Asn Gly Gln Ile Val Ser Asp
        50                  55                  60

Ser Glu Val Ile Thr Ser Thr Glu Ala Lys Ala Ala Ile Leu Ser
65                  70                  75                  80

Val Ile Ser Ser Tyr Pro Lys Glu Ile Arg Glu Gln Leu Asn Gly Arg
                85                  90                  95

-continued

```
Ile Glu Arg Gly Phe Thr Asp Asn Pro Asp Val Asp Glu Ala Ala Arg
            100                 105                 110
Cys Ile His Ser Ala Arg Leu His Asn Ile Thr Thr Thr Ala Leu Arg
        115                 120                 125
Lys Lys Pro Leu Leu Val His Glu Asn Val Ser Asn Asp Met Glu Arg
    130                 135                 140
Phe Leu Asn Glu Lys Phe Leu Gly Tyr Lys Ile Arg Leu Thr Cys Ser
145                 150                 155                 160
Lys Asn Val Ala His Asn Asn Ala Ala Leu Arg Arg Val Leu Arg
                165                 170                 175
Phe Tyr Met Arg Asp Lys Val Gly Tyr Arg Lys Asp Asp Ile Pro
            180                 185                 190
Glu Gly Tyr His Val Lys Asn Lys Asp Val Gly Ala Ser Gly Met Asp
            195                 200                 205
Val Ile Ala Asp Glu Leu Thr Asp Val His Cys Cys Thr Pro Asp Leu
        210                 215                 220
Asp Phe Arg Asp His Ile Arg Leu Glu Arg Leu Lys Lys Tyr Ile Tyr
225                 230                 235                 240
Ser His Val Cys Pro Thr Ser Lys Asp His Gly Ile Ile Cys Glu Gly
                245                 250                 255
Phe Arg Glu Gly Ser Thr Lys Tyr Arg Cys Glu Asn Ile Gly Gln Gln
            260                 265                 270
Cys Tyr Ile Lys Ala Pro Thr Leu Thr Phe Val His Ser Ala Tyr Asp
            275                 280                 285
Ile Thr Ala Ala Gly Ile Val Asp Cys Met Ile Ala Ala Asn Ala His
        290                 295                 300
His Ala Ile Met Cys Leu His Phe Pro Ser Ala Ile Leu Ser Gly Ser
305                 310                 315                 320
Thr Ser Gly Lys Asp Asp Leu Leu Gln Tyr Lys Trp Asp Ile Val Val
                325                 330                 335
Glu Asp Gly Ile Lys Tyr Tyr Lys Gln Lys Phe Leu Asn Asp Thr Gln
            340                 345                 350
Ala Ser Tyr Val His Arg Leu Asp Val Tyr Leu Asp Lys Phe Leu Thr
        355                 360                 365
Lys Val Val Leu Gly Ser Asp Lys Arg Phe Tyr Met Phe Glu Ile Thr
    370                 375                 380
Glu Met Phe Gly Ser Val Ala Ile Ile Glu Val Phe Arg Arg Glu Lys
385                 390                 395                 400
Asp Phe Ile Ala Gly Ser Lys Leu Thr Phe Asn Ile Pro Arg Thr Glu
            405                 410                 415
His Pro Asn Thr Val Thr Ile His Thr Trp Glu Tyr Val Thr Gly Tyr
        420                 425                 430
Glu Ser Leu Phe Lys Gly Arg Asn Gly Leu Lys Ser Gly Val Met Arg
    435                 440                 445
Pro Val Ser Ile Glu Val Pro Glu Glu Phe Phe Leu Ser Val Phe Lys
    450                 455                 460
Tyr Gly Met Thr Val Asp Ser Asn Lys Phe Val Tyr Asp Gly Leu Leu
465                 470                 475                 480
Lys Ser Gly Val Gly Ile Ala Ala Arg Arg Asn Ile Gly Thr Thr
                485                 490                 495
Met Val Asp Pro Ser Ser Pro Ile Pro Val Arg Lys Leu Gln Thr Phe
            500                 505                 510
Ile Val Thr Met Tyr Met Leu Leu Tyr Gln Glu Lys Trp Glu Ala Thr
```

-continued

```
            515                 520                 525
Gln Gly Leu Val Thr Met Lys Met Leu Ala Asp Gln Tyr Arg Thr Arg
        530                 535                 540

Ser Ser Lys Asn Gly Ile Val Arg Phe Leu Thr Asn Val Phe Ser Pro
545                 550                 555                 560

Asp Lys Val Gly Glu Thr Gln His Pro Ser Thr Tyr Asp Leu Gly
                565                 570                 575

Lys Leu Gly Phe Ser His Ser Glu Asp Asn Lys Phe Val Cys Asp Arg
            580                 585                 590

Asn Leu Asn Thr Glu Glu Arg Ser Arg Leu Ser Gln Phe Glu Arg Leu
        595                 600                 605

Val Gln Trp Phe Arg Glu Phe Ser Arg Val His Arg Lys Cys Pro Ile
    610                 615                 620

Val Val His Asp Ser Thr His Met Leu Glu Tyr Val Leu Asp Ile Pro
625                 630                 635                 640

Asp Met Val Val Gln Asn Ile Lys Ser Leu Arg Asp Asp Leu Thr Leu
                645                 650                 655

Ser Asn Leu Cys Asp His Asp Phe Asp Ala Tyr Leu Pro Ser His Ile
            660                 665                 670

Glu Val Asn Asp Ala Lys Cys Thr Lys Asp Leu Thr Val Ile Gln Val
        675                 680                 685

Pro Gly Asp Gly Asn Cys Leu Tyr Tyr Cys Phe Val Lys Ala Cys Leu
    690                 695                 700

Tyr Arg Gly Ile Ser Val Cys Asp Leu Lys Ser Arg Leu Arg Asp Ser
705                 710                 715                 720

Pro Tyr Phe Leu Glu Val Ala Lys Leu Ala Arg Asp Ser Gly Glu Asp
                725                 730                 735

Glu Phe Leu Asp Ser Leu Glu Arg Asp Gly Val Tyr Gly Asn Lys Phe
            740                 745                 750

Thr Leu Ile Leu Ile Ser Lys Thr Phe Asn Val Asn Ile Cys Val His
        755                 760                 765

Leu Lys Gly Gly Arg Glu Leu Ile Thr His Phe Ile Ser Asn Lys Gly
    770                 775                 780

Ser Arg Phe Ile His Leu Gln Leu Glu His Ser His Tyr Ser Leu Leu
785                 790                 795                 800

Val Pro Cys Ile Lys Ala Gly Leu Ile Asp Glu His Val Leu Cys His
                805                 810                 815

Gly Ala Leu Ser Met Val Val Pro Thr Ala His Asp Tyr Arg Arg Leu
            820                 825                 830

Val Asp Leu Tyr Lys Ile Tyr Thr Arg Asp Gly Thr Ile Ala Ser Tyr
        835                 840                 845

Phe Asn Ile Phe Asn Asn Ser Tyr Lys Gly Pro Phe Leu Asn Val Tyr
    850                 855                 860

Glu Leu Gly Phe Met Glu Ile Ala Ser Ser Leu Glu Ile Pro Ser Ser
865                 870                 875                 880

Ser Gly Asn Lys Phe Leu Ile Thr Asp Val Trp Leu His His Cys Ile
                885                 890                 895

Lys Ala Leu Arg Val Leu Asp Pro His Ser Asn Val Ile Val Leu Arg
            900                 905                 910

Ser Ser Asn Thr Ser Arg Ile Pro Asp Arg Tyr Gly Val Cys Asp Phe
        915                 920                 925

Thr Met Asp Ser Glu Phe His Glu Glu Ser Phe Cys Leu Ser Thr Thr
    930                 935                 940
```

```
Leu Ser Asp Val Leu Asn Leu Gly Ile Tyr Ser Gln Cys Met Val Val
945                 950                 955                 960

Phe Ser Asp Leu Ser Arg Val Pro Leu Lys Pro Phe Ala Pro Gly Phe
                965                 970                 975

Arg Thr Arg Thr Ser Val Ala Glu Arg Ser Asn Lys Ile Leu Leu Ala
            980                 985                 990

Trp Ser Ala Leu Ser Ser Gly Gly Thr Ala Val Phe Arg Val Phe Arg
        995                 1000                1005

Pro Glu Glu Val Pro Glu Ser Leu Asn Met Leu Thr Thr Leu Phe
1010                1015                1020

Glu Asp Ile Arg Phe Phe Lys Pro Lys Ala Ile Ser Thr Ser Ile
1025                1030                1035

Val Asp Gly Tyr Leu Leu Cys Ser Gly Lys Arg Ser His Pro Gly
1040                1045                1050

Ser Glu Phe Ser Ile Thr Ser Glu Val Arg Asn His Phe Tyr Thr
1055                1060                1065

Val Asn Val Glu Asn Phe Tyr Lys Gln Thr Leu Glu Glu Ser Glu
1070                1075                1080

Val Ser Asn Tyr Val Lys Asp Leu Cys Gly Leu Tyr Ala Gly Gly
1085                1090                1095

Gly Phe Val Lys Pro Thr Arg Lys His Ser Tyr Asn Arg Ser Phe
1100                1105                1110

Val Leu Asp Arg Ser Leu Ile Leu Ser Lys Leu Met Glu Phe Ser
1115                1120                1125

Ser Ser Val Ser Phe Gly Leu Phe Gly Arg Lys Phe Ser Thr Tyr
1130                1135                1140

Lys Leu His Val Gly Cys Asp Thr Lys Leu Lys Phe Cys Asn Arg
1145                1150                1155

Ser Ile Glu Glu Ile Leu Asp Ser Gln Cys Leu His Cys Lys Tyr
1160                1165                1170

Ser Lys Tyr Asp Phe Asn Ser Leu Arg Ser Val Ser Asp Leu Ala
1175                1180                1185

Ser Phe Ala Thr Arg Glu Arg Ala Val Val Val Glu Thr Phe Asp
1190                1195                1200

Asp Cys Gly Asp Tyr Val Ser Ile Ile Ser Phe Phe His Lys Leu
1205                1210                1215

Tyr Ser Met Cys Phe Lys Asp Leu Arg Val Val Ser Asp Cys Phe
1220                1225                1230

Leu Asn Asn Val Val Leu Lys Ser Phe Leu Ala Tyr Ala Arg Cys
1235                1240                1245

Tyr Ser Asp Val Glu Ile Ser Leu Cys Gln Leu Lys Gly Arg Leu
1250                1255                1260

Leu Val Asp Ile Thr Cys Arg Ser Ser Trp Tyr Asn Gly Cys Glu
1265                1270                1275

Phe Gly Asp Phe Glu Leu Val Ser Cys Asn Arg His Asp Tyr Asp
1280                1285                1290

Thr Ala Phe Val Glu Val Leu Ile Gln His Ala Met His Asn Gln
1295                1300                1305

Arg Tyr Asn Asn Glu Thr Ile Val Ile Asn Ser Arg Ala Asp Ala
1310                1315                1320

Ile Arg Ala Gly Leu Ser Val Arg Lys Phe Lys Pro Cys Gly Asp
1325                1330                1335
```

-continued

| | | | | | | | | | | | |
|---|---|---|---|---|---|---|---|---|---|---|---|
| Val | Leu | Asp | Asp | Leu | Asn | Lys | Ser | Val | Lys | Tyr | Lys | Pro | Lys | Phe |
| | 1340 | | | | 1345 | | | | 1350 | | |

Val Thr Tyr Asn Thr Glu Ser Leu Val Asn Ser Ile Lys Ala Ile
     1355                        1360                        1365

Val Gly Val Gly Asp Glu Thr Thr Lys Glu Pro Thr Asp Asn Ser
     1370                        1375                        1380

Val Val Glu Lys Pro Val Val Phe Glu Lys Val Asp Ser Pro
     1385                        1390                        1395

Asn Leu Asp Asp Arg Ile Lys Ala Val Tyr Glu Tyr Arg Ser Tyr
     1400                        1405                        1410

Met Gly Arg Glu Leu Ser His Ser Asn Asp Val Leu Glu Lys Thr
     1415                        1420                        1425

Val Ser Asn Leu Leu Arg Phe Thr Glu Thr Arg Asp Pro Lys Arg
     1430                        1435                        1440

Leu Asn Glu Met Tyr Phe Pro Asn Ser Ser Phe Leu Ser Asp Glu
     1445                        1450                        1455

Met Lys Leu Lys Asp Ser Val Gly Ile Ile Thr Cys Asn Gly Lys
     1460                        1465                        1470

Ile Leu Lys Asn Ser Glu Pro Ile Val Gln Phe Asp Asp Ile Ser
     1475                        1480                        1485

Ala Val Tyr Asp Ile Val Asn Gly Ser Val Val Asp Lys Ser Asp
     1490                        1495                        1500

Tyr Phe Lys Met His Arg Gly Lys Thr Thr Lys Gln Val Gly Gly
     1505                        1510                        1515

Phe Ala Ile Tyr Thr Ser Leu Val Ala His Asn Gln Val Glu Ser
     1520                        1525                        1530

Ile Leu Lys Ala Val Asp Cys Val Tyr Ala Ser Glu Lys Ile Asn
     1535                        1540                        1545

Asp Leu Ser Ala Ile Ser Ile Asp Trp Val Gln Ala Val Ala Gly
     1550                        1555                        1560

Ala Gly Lys Thr Thr Leu Leu Val Glu Thr Phe Leu Ile Thr Asp
     1565                        1570                        1575

Leu Val Val Cys Pro Thr Val Glu Asn Arg Asp Ser Ile Arg Leu
     1580                        1585                        1590

Arg Ile Lys Arg Arg Tyr Pro Asp Leu Asp Pro Lys Glu Val Asp
     1595                        1600                        1605

Cys Arg Val Arg Thr Ile Asn Gly Tyr Leu Val Asp Phe Ser Thr
     1610                        1615                        1620

Lys Leu Ala Lys Val Thr Leu Asn Glu Asn Thr Arg Leu Leu Val
     1625                        1630                        1635

Asp Glu Ala Ile Met Tyr His Ala Gly Cys Leu Phe Val Leu Cys
     1640                        1645                        1650

Met Ile Tyr Asn Ile Arg Arg Met Phe Cys Val Gly Asp Lys Lys
     1655                        1660                        1665

Gln Ile Pro Phe Val Ser Arg Ile Asp Phe Lys Leu Asn Tyr Glu
     1670                        1675                        1680

Lys Leu Cys Asp Phe Val Asn Thr Glu Ala Arg Pro Leu Ala Arg
     1685                        1690                        1695

Thr Phe Arg Ser Pro Pro Asp Val Thr Tyr Arg Met Gln Gln Ile
     1700                        1705                        1710

Tyr Gly Lys Ser Leu Lys Gly Leu Thr Ile Gln Cys Leu Ser Lys
     1715                        1720                        1725

Asn Gln Asp Thr Ser Pro Ser Val Ser Lys Leu Val Ile Thr Lys

-continued

```
            1730                1735                1740
Asn Tyr Arg Phe Gly Gln Asn Phe Ile Arg Glu Val Phe Glu Lys
            1745                1750                1755
Asp Lys Ile Asp Phe Asp Gly Lys Asn Leu Arg Ile Leu Phe Phe
            1760                1765                1770
Leu Arg Glu Asp Met Leu Ser Phe Tyr Gly Asn Gly Gly Met Ile
            1775                1780                1785
Phe Thr Asp Cys Cys Ser Thr Ile His Gln Phe Gln Gly Ser Asp
            1790                1795                1800
Ala Glu Tyr Val Val Val Met Arg Leu Thr Tyr Ala Glu Lys Ser
            1805                1810                1815
Ile Phe Met Asp Glu Arg Gln Cys Leu Val Ala Leu Thr Arg His
            1820                1825                1830
Thr Lys Arg Met Val Tyr Val Ser Val Asn Glu Gly Thr Asp Val
            1835                1840                1845
Leu Thr Arg Trp Ile Asn Met Pro Val Val Glu Ser Met Leu Val
            1850                1855                1860
Pro His Leu Ser Leu Ser Gly Gly Gly Thr Thr Thr Pro Ser Arg
            1865                1870                1875
Tyr Val Thr Tyr Arg Ser Ile Pro Ser Val Asp Leu Met Lys Gly
            1880                1885                1890
Asp Lys Cys Val Arg Val Gly Tyr His Pro Arg Ser Asp Ile Ile
            1895                1900                1905
Leu Asp Lys Arg Asp Thr Leu Thr Ala Val Leu Asn Lys Ile Ala
            1910                1915                1920
Asp Ala Arg Pro Lys Gly Asn Leu Val Val Ser Ser Ala Val Leu
            1925                1930                1935
Asp Lys Phe Asn Gln Gln Arg Leu Lys Pro Leu Leu Lys Ser Ile
            1940                1945                1950
Val Gly His Ser Asn Ile Phe Cys Ala Gly Val Asn Ser Asn Ile
            1955                1960                1965
Asn Ser Thr Val Phe Glu Val Met Gln Leu Asn Ala Val Asp His
            1970                1975                1980
Val Pro Asn His Phe Ile Asp Pro Ile Phe Asp Asp Asp Val Val
            1985                1990                1995
Arg Ser Ala Asp Ile Gly Tyr Lys Pro Tyr Arg Gln His Asp Asn
            2000                2005                2010
His Asp Pro Val Leu Ser Asp Tyr Gly Phe Asp Asp Lys Phe Ala
            2015                2020                2025
Val Ile Gln Asn Phe Leu Cys Thr Thr Phe Pro Asn Ser Cys Tyr
            2030                2035                2040
Val Pro Asn Tyr Met Asp Ala Trp Ile Thr Tyr Asn Leu Asp Leu
            2045                2050                2055
Asp Leu Ala Ile Asp Asp Ile Val Ile Asn Val Ile Lys Phe Ala
            2060                2065                2070
Thr Ile Asp Arg Thr Tyr Asp Cys Met Ile Pro Arg Leu Ser Phe
            2075                2080                2085
Cys Ser Pro Val Val Arg Lys Ala Cys Leu Val Glu Ser Leu Ile
            2090                2095                2100
Ala Val Gln Lys Arg Asn Arg Asn Val Pro Gln Leu Ser Ser Glu
            2105                2110                2115
Val Ser Pro Tyr Val Met Ala Asp Gln Leu Phe Asp Ser Leu Arg
            2120                2125                2130
```

-continued

Ser Leu Leu Asp Glu Arg Tyr Tyr Gln Glu Val His Tyr Gly Pro
2135                2140                2145

Ala Glu Leu Ala Ala Trp Leu Asn Asp Gln Lys Gly Ser Val Val
2150                2155                2160

Asp Glu Val Ile Gly Glu Tyr Cys Ile Tyr Ser Thr Ala Val Glu
2165                2170                2175

Arg Tyr Gln Leu Ile Thr Lys Asn Ser Pro Lys Pro Thr Leu Ser
2180                2185                2190

Asp Glu Ala Tyr Met Glu Phe Ala Ala Pro Gln Val Val Leu His
2195                2200                2205

Gln Thr Lys Asp Ile Asn Ala Val Phe Cys Val Ile Trp Arg Gly
2210                2215                2220

Ile Lys Thr Val Val Gln Ser Met Leu Arg His His Asn Asn Ile
2225                2230                2235

Phe Met Phe Ala Asp Met Asp Pro Asp Ser Phe Ala Asp Leu Leu
2240                2245                2250

Thr Glu Lys Val Ser Thr Lys Val Gln Glu Thr Phe Asp Ser Leu
2255                2260                2265

Glu Ile Asp Ile Lys Lys Tyr Asp Lys Ser Gln Asp Leu Lys Val
2270                2275                2280

Leu Leu Leu Glu Cys Lys Leu Leu Arg Tyr Phe Gly Val Ser Glu
2285                2290                2295

Glu Leu Val Ile Ile Trp Phe Lys Ser His Val Glu Ser Ile Val
2300                2305                2310

Lys Asp Arg Arg Ser Gly Leu Lys Phe Lys Val Gln Val Gln Arg
2315                2320                2325

Arg Ser Gly Asp Gly Gly Thr Phe Ile Gly Asn Thr Leu Phe Leu
2330                2335                2340

Ile Val Leu Cys Ala Arg Asn Phe Asp Leu Arg Lys Leu Lys Leu
2345                2350                2355

Ala Val Phe Ser Gly Asp Asp Ser Leu Leu Val Gly Glu Lys Arg
2360                2365                2370

Asp Leu Gln Cys Asp Ser Gln Asn Phe Ser Asp Leu Phe Asn Leu
2375                2380                2385

Asp Val Lys Phe Phe Pro Asn Phe Lys Tyr Tyr His Phe Cys Ser
2390                2395                2400

Lys Phe Leu Ile Ala Val Glu Asp Arg Trp Tyr Phe Ile Pro Asp
2405                2410                2415

Pro Val Lys Leu Cys Ile Arg Leu Ala Arg Leu Asp Leu Val Asn
2420                2425                2430

Trp Gly His Ile Glu Glu Tyr Arg Ile Ser Leu Lys Asp Thr Thr
2435                2440                2445

Lys Tyr Tyr Cys Asp Asp Ser Ile Val Arg Glu Leu Ser Lys Ala
2450                2455                2460

Val Cys Asp Arg Tyr Pro Val Ala Val Asp Pro Ala Glu Val Phe
2465                2470                2475

Arg Val Val Cys Ser Ile Val Ser Ser Lys Asp Glu Phe Arg Leu
2480                2485                2490

Leu Phe Glu Glu Pro Leu Ala Cys Leu Pro Glu Gly Asn Leu Leu
2495                2500                2505

Pro Val Ile Asn
2510

<210> SEQ ID NO 7
<211> LENGTH: 263
<212> TYPE: PRT
<213> ORGANISM: Citrus Leprosis virus

<400> SEQUENCE: 7

Met Ser Ile Val Thr Phe Thr Leu Thr Asp Pro Ser Ser Ala Leu Ile
1               5                   10                  15

Ala Glu Ile Met Gln Ala Ile Glu Arg His Asn Val Ser Val Pro Glu
            20                  25                  30

Gly Leu Arg Asp Ile Ser Lys Pro Thr Lys Lys Gln Gln Ser Gln
        35                  40                  45

Pro Gln Gln Leu Ser Arg Ala Ser Ala Arg Pro Gln Gln Leu Gln Pro
    50                  55                  60

Gly Pro Ser Gly Tyr Gln Ala Lys Lys Pro Ala Lys Gln Lys Ala Glu
65                  70                  75                  80

Val Val Lys Pro Lys Gln Lys Gln Leu Ala Pro Pro Ile Asn Lys Lys
                85                  90                  95

Ala Ala Lys Ala Lys Leu Tyr Gly Leu Glu Gln His Cys Pro Lys Tyr
            100                 105                 110

Ala Glu Ala Lys Gly Leu Gln Lys Gln Ile Gly Met Thr Tyr Tyr Lys
        115                 120                 125

Ile Ser Glu Pro Tyr Ala Leu Pro Asp Phe Lys Val Met Glu Ala Ser
    130                 135                 140

Glu Asp Leu Val Ala Val Ser Glu Lys Asp Pro Met Gly Ser Phe Glu
145                 150                 155                 160

Lys Arg Leu Tyr Ser Met Gly Phe Pro Lys Arg Pro Ile Lys Asn Val
                165                 170                 175

Val Pro Val Phe Glu Phe Ser Asp His Tyr Ile Val Phe Phe Pro
            180                 185                 190

Gly Ser Asn Ala Glu Ile Val Lys Asn Val Pro Lys Asp Ser Val Ser
        195                 200                 205

Asp Tyr Ala Glu Ala Gln Leu Ala Ala Leu Leu Ala Ala Arg Gln Gln
    210                 215                 220

Ile Asn Gln Ile His Glu Leu Gly Asp Ile Leu Pro Thr Asn Tyr Leu
225                 230                 235                 240

Asn Val Leu Asp Ser Gly Thr Gln Asp Val Val Val Ser Asp Glu Glu
                245                 250                 255

Asp Asp Ser Asp Ser Ala Gln
            260

<210> SEQ ID NO 8
<211> LENGTH: 4975
<212> TYPE: DNA
<213> ORGANISM: Citrus Leprosis virus

<400> SEQUENCE: 8
gataaatcta atcaatctat tgtattgttc taggctaata actctcaatt attagtgaac    60
attacaatgc tgaactggtc tacgattgag tgggacagtt tctggcaaca gcacgattgc   120
ggttgcttta cgttcgagtg tgattttatt acctctatag atccactcgt gcatgattac   180
gcgatttatc attctttatc tcaaaagact gttctcgaga tgcttcagac gcacttggtt   240
gccgggccag atgcatctga aacaattcga agacaagttg cctttctcat ttatgacttt   300
cacaggttat cctgtaattg tgataaatgt tatggggatt gcaatgctac cactaccggt   360

```
agattcaagg tggtcgatcg tgttttgaac gatcacattg aattcggtat tatgcgtcgt    420
caagacctaa taccgatact gcataatctt gagacttaat tgtcatctcg ctagcacatg    480
tttgtggggt atgacgagta ctaattcaag gtgcggggct acgccttatg attttgtcga    540
ctttcgcgtg ttgacaactt cattactggt cttaaaccgc ttaatcccaa tgcggggact    600
tgtgtttgtc atttgccata cttcacaaac atgtgctagc aagtgaatac atatgtttgt    660
acactgtatc atttgtttca tgagctgttt cagtcgggca tagtataaat aagagcgcaa    720
gggaagggac tgcgcatact aatacggttg ttcgagctca tgttgcttgt gaatcatagg    780
tagtcaacgc aggatttgtc tgcaatatct acggatcaag ggaaattgcg tggagatcat    840
gtacggagac ggcactacgc tgtataggat cttgagggat caaaccagcc ttaatccgct    900
tgccccaatg cggggacgtg tatgtattga agcgcggttt cctacgagaa gcagattgcg    960
ttgacatatt cttgactatc atgattgatg gagcttttgt ttaaccacgt agtacttgga    1020
cggaacggtg catcgccttg aggtaaggtc ataaagccga ttgccccaat gcggggacgt    1080
ccattgtatg aagcggggcg acaaagtttt cacttacagt ttacatcact tgtatttcac    1140
tttaagtata ttggtcattt gattgctatt tgacttgtca tatagttatc acttgaccct    1200
tgaactaata cagcgagtat tgaacgctgg tacgtatact attagggttt agtcctaata    1260
gtattcattt tcaaccactt tcaatattct ttgttttcat tgaatattga taattgttag    1320
atttattgct agggcttagc cctagcagta ttcatcttca accaccttca atattctttg    1380
cttatgccac gagtcacata tgatttgaga tgaattgtag ttgtgactac atgtaaccat    1440
aattgatttg ggagcgtagg cttccaggtt gatgccgacc ggtttgtata tattgtaaat    1500
gttgtaaata cagtttcata cgtacgtgcg gaacagtttg ctgtaaatac gagagcctac    1560
agcaaattaa gctaaaatag tattgtcaaa tggcgctatt tcagcttttt agtttcttaa    1620
atgttacgtt ggggctcgta tccaacatct acaaagtac gggacacctt agtattgata    1680
aagcctgttc ggggtacagt actgaggcgt tcaaggggcgt ttgtctaccc tcgtatagtt    1740
atgtcaaggt tgatagacat atcttaacga aggatgatag gtactatctt ggttacgcta    1800
aggccacaaa tcgtgaatac cagttgtata gtttacatat tggtacctac gatttgttcg    1860
gtagtgatat catgtcatgt ggtgctaggg gctatgctct gggtctccac aacggagacc    1920
ttgagttggt tcttaattat tgccgtaagg tcgatgggca gaagcatatt ggtgaagtgt    1980
tccaaagttg tagattcgtt gagtatagcg aacatatgat ttctggaatt gttcactcga    2040
tacctaagga cttaatggaa gagtttagtc caataggcaa ggtaccgtat ttcggtatca    2100
tgccttttag gactgagtgc gcagatcaat gttctactaa gcaagcattt tatgcaatgg    2160
atgcttatcc ttttttataac attggctact ggtttccatt atgtgctgac aagtatatcc    2220
cactatgtta cagcggtcgt acggatccat gtccacttgg atatgaggag aggcttataa    2280
aagtccactc atatatggag gggtttgagt ctggtatgaa gaccgtttgt aaatctggtg    2340
aatatatttt tccagcctgg tactcaggac aatcagagat atatgatacg gttgttaaac    2400
cgtatattgt taatgtccct gaatattgtg ggcgatttag tcgctctgat aagtccttgg    2460
tttattccag gttggttttt agagggacta tcttttctgg gcttaaggtt attacattag    2520
atggtattga ttatttgacc acagatttct gtgtcaatta ttctatgcat cattatgtaa    2580
aaccgctggt ttttgaaagg atgcggaagt cctttatttg cacctcgtct ggttgtttat    2640
ataaaggctt tgatgttaat catcttcatg acatttgtac acctaaattg gttgtgaaac    2700
gtcatgaggc tttgatttct tccttttctt tcataaacac tctcggtacc aaagtgggtg    2760
```

```
ctgttcctta tgattttgat gggaatatca tacagttcat cgacgttttt agcatcgatg    2820
ggttttatgt ttactcgttg agtcacaaga agatccaaac tctcacagta atgctcgttc    2880
agtctgaaga agagtggtat atgaagttgt tgcattttgt tgcggacgac atacttaggg    2940
aatgtttgag tacagtcttt aaagtattgt tttccgctat tagtgcttgc ctatccttca    3000
ttattgatgt tggtggatgt tgcttccgcc aattcatctt tgtttgtttg gattctgtga    3060
ttttgttatt gctactgctc ccgaattaca cccatttaac gttatcctta ggatttacgc    3120
tgaatgctta catacagttg gtgtattatg agagctgttg ttttagagct tatcgcgaca    3180
tagctgaaac cattgatttg taaatcaatg gtgaatttta tgttgagatg gctcttttcta   3240 ccaataacaa ttcttctcac gttggtgctg acgattttt ggaattggag aatatcttat     3300
cctccgagta taatgaggag gggatattca agacttcaaa gaccgtttgc attcggactg    3360
acaagcgtat tggcgttgga tttctgacac cgaacgatat gatttctcgt ttggttgggt    3420
tcataaaccg taaagctgaa gacgctgggg ttagatctgt ggagtctttt aggcagatat    3480
ctgatgtcgt gcttataatt gtgccgcaga tagcgctccc ggccgagctg tcgctaaagc    3540
ttgtcgattc agctaatata ctagaggctg ttaatgacca agaggtcact gtcaatagta    3600
ctggtggtcc atgtgttgtt gtcatgaact gtgcccattc gattccgaat gaggacagga    3660
ctcatgttaa tggatctgaa gttcacaggc ggcttggtat acagtatcaa gttgactgtg    3720
ataatatttc aggtcgtgta acaacctttt cgatcactgc actatggcgc gaggcttttt    3780
cgtttcgacc atccttttat aaggtgtcgg atcctcttgt ggtcccaata tctgtgggct    3840
ttcgcaaggc agttattgcg aaatcacatg cagatttaca aaggtccata ggtagaggtt    3900
tgattgtcac tcaccactcc tctcaatcgt cagtcacgtc ggagagtccg attgacttga    3960
cggttaagaa gagtactggt cttaaaatac gagacaagag tgaggatgat aatcaaagaa    4020
aacatcctgt tccattgacg tcaagtaata ataagcttaa aactttaaga gtatcgacga    4080
cgccaattgt gaatggacgc tcaacttcta caagcgaata acgcctctt gaggcgcgca     4140 gctaacgtta ggcaaagata taagatgttg gcaacggaaa gtttcgtcgc tgacatcaag    4200
cagattttgc ttaggtttat acaaaaacct aacgttataa ttatgtatat cagtgttttg    4260
gttctatttg ctgcgcatat agactcaaac actcatgata ttcttgatga tttggctgcg    4320
cagtttccta ataacacctt tattgagtgg gcgaagagta acttcttcag gatctgtggt    4380
gctctggtat ttataccagt tattatagat actgaagaga agcacaggaa ttaccttgct    4440
ttagttatat tcgttttcct tatgggtttt ccacaaagat cgattatgga gtatttcata    4500
tattccatat cttccatgt gtatgctaag gctaaacacc ctgtcactcg gatttttatc      4560
attggggcag ccgtgttttc atgcgttatg tttggcatat ttaccaacga acaattgagg    4620
aagctttatg ctgaactccc gaaggtgcca actcatcccg tagctgtgaa cagggttgaa    4680
aaagttgcca ataggcttc tagggtgtct actgaaggca ccgtcaactt tggttgacac     4740
ctactggtgt tatgcggagg gttttcttgc ggttctttcc ctcactatat gttttgaatc    4800
gctaatctct ggtactttt tttttgtatt gaagattatt tgaactatgt tcagtccggt     4860
cgttgtcagc tgggcgaggt tgaaattcct caagtttgat taatttctag tctcttctag    4920
ctggtggtgt accactttt ctttttgat tttctttct tttgtcttta tgaca            4975
```

<210> SEQ ID NO 9
<211> LENGTH: 130
<212> TYPE: PRT

-continued

<213> ORGANISM: Citrus Leprosis virus

<400> SEQUENCE: 9

Met Leu Asn Trp Ser Thr Ile Glu Trp Asp Ser Phe Trp Gln Gln His
1               5                   10                  15

Asp Cys Gly Cys Phe Thr Phe Glu Cys Asp Phe Ile Thr Ser Ile Asp
            20                  25                  30

Pro Leu Val His Asp Tyr Ala Ile Tyr His Ser Leu Ser Gln Lys Thr
        35                  40                  45

Val Leu Glu Met Leu Gln Thr His Leu Val Ala Gly Pro Asp Ala Ser
    50                  55                  60

Glu Thr Ile Arg Arg Gln Val Ala Phe Leu Ile Tyr Asp Phe His Arg
65                  70                  75                  80

Leu Ser Cys Asn Cys Asp Lys Cys Tyr Gly Asp Cys Asn Ala Thr Thr
                85                  90                  95

Thr Gly Arg Phe Lys Val Val Asp Arg Val Leu Asn Asp His Ile Glu
            100                 105                 110

Phe Gly Ile Met Arg Arg Gln Asp Leu Ile Pro Ile Leu His Asn Leu
        115                 120                 125

Glu Thr
    130

<210> SEQ ID NO 10
<211> LENGTH: 537
<212> TYPE: PRT
<213> ORGANISM: Citrus Leprosis virus

<400> SEQUENCE: 10

Met Ala Leu Phe Gln Leu Phe Ser Phe Leu Asn Val Thr Leu Gly Leu
1               5                   10                  15

Val Ser Asn Ile Tyr Asn Ser Thr Gly His Leu Ser Ile Asp Lys Ala
            20                  25                  30

Cys Ser Gly Tyr Ser Thr Glu Ala Phe Lys Gly Val Cys Leu Pro Ser
        35                  40                  45

Tyr Ser Tyr Val Lys Val Asp Arg His Ile Leu Thr Lys Asp Asp Arg
    50                  55                  60

Tyr Tyr Leu Gly Tyr Ala Lys Ala Thr Asn Arg Glu Tyr Gln Leu Tyr
65                  70                  75                  80

Ser Leu His Ile Gly Thr Tyr Asp Leu Phe Gly Ser Asp Ile Met Ser
                85                  90                  95

Cys Gly Ala Arg Gly Tyr Ala Leu Gly Leu His Asn Gly Asp Leu Glu
            100                 105                 110

Leu Val Leu Asn Tyr Cys Arg Lys Val Asp Gly Gln Lys His Ile Gly
        115                 120                 125

Glu Val Phe Gln Ser Cys Arg Phe Val Glu Tyr Ser Glu His Met Ile
    130                 135                 140

Ser Gly Ile Val His Ser Ile Pro Lys Asp Leu Met Glu Glu Phe Ser
145                 150                 155                 160

Pro Ile Gly Lys Val Pro Tyr Phe Gly Ile Met Pro Phe Arg Thr Glu
                165                 170                 175

Cys Ala Asp Gln Cys Ser Thr Lys Gln Ala Phe Tyr Ala Met Asp Ala
            180                 185                 190

Tyr Pro Phe Tyr Asn Ile Gly Tyr Trp Phe Pro Leu Cys Ala Asp Lys
        195                 200                 205

Tyr Ile Pro Leu Cys Tyr Ser Gly Arg Thr Asp Pro Cys Pro Leu Gly

```
            210                 215                 220
Tyr Glu Glu Arg Leu Ile Lys Val His Ser Tyr Met Glu Gly Phe Glu
225                 230                 235                 240

Ser Gly Met Lys Thr Val Cys Lys Ser Gly Glu Tyr Ile Phe Pro Ala
                245                 250                 255

Trp Tyr Ser Gly Gln Ser Glu Ile Tyr Asp Thr Val Val Lys Pro Tyr
                260                 265                 270

Ile Val Asn Val Pro Glu Tyr Cys Gly Arg Phe Ser Arg Ser Asp Lys
                275                 280                 285

Ser Leu Val Tyr Ser Arg Phe Gly Phe Arg Gly Thr Ile Phe Ser Gly
                290                 295                 300

Leu Lys Val Ile Thr Leu Asp Gly Ile Asp Tyr Leu Thr Thr Asp Phe
305                 310                 315                 320

Cys Val Asn Tyr Ser Met His His Tyr Val Lys Pro Leu Val Phe Glu
                325                 330                 335

Arg Met Arg Lys Ser Phe Ile Cys Thr Ser Ser Gly Cys Leu Tyr Lys
                340                 345                 350

Gly Phe Asp Val Asn His Leu His Asp Ile Cys Thr Pro Lys Leu Val
                355                 360                 365

Val Lys Arg His Glu Ala Leu Ile Ser Ser Phe Ser Phe Ile Asn Thr
                370                 375                 380

Leu Gly Thr Lys Val Gly Ala Val Pro Tyr Asp Phe Asp Gly Asn Ile
385                 390                 395                 400

Ile Gln Phe Ile Asp Val Phe Ser Ile Asp Gly Phe Tyr Val Tyr Ser
                405                 410                 415

Leu Ser His Lys Lys Ile Gln Thr Leu Thr Val Met Leu Val Gln Ser
                420                 425                 430

Glu Glu Glu Trp Tyr Met Lys Leu Leu His Phe Val Ala Asp Asp Ile
                435                 440                 445

Leu Arg Glu Cys Leu Ser Thr Val Phe Lys Val Leu Phe Ser Ala Ile
450                 455                 460

Ser Ala Cys Leu Ser Phe Ile Ile Asp Val Gly Gly Cys Cys Phe Arg
465                 470                 475                 480

Gln Phe Ile Phe Val Cys Leu Asp Ser Val Ile Leu Leu Leu Leu Leu
                485                 490                 495

Leu Pro Asn Tyr Thr His Leu Thr Phe Ile Leu Gly Phe Thr Leu Asn
                500                 505                 510

Ala Tyr Ile Gln Leu Val Tyr Tyr Glu Ser Cys Cys Phe Arg Ala Tyr
                515                 520                 525

Arg Asp Ile Ala Glu Thr Ile Asp Leu
                530                 535

<210> SEQ ID NO 11
<211> LENGTH: 297
<212> TYPE: PRT
<213> ORGANISM: Citrus Leprosis virus

<400> SEQUENCE: 11

Met Ala Leu Ser Thr Asn Asn Ser Ser His Val Gly Ala Asp Asp
1               5                   10                  15

Phe Leu Glu Leu Glu Asn Ile Leu Ser Ser Glu Tyr Asn Glu Glu Gly
                20                  25                  30

Ile Phe Lys Thr Ser Lys Thr Val Cys Ile Arg Thr Asp Lys Arg Ile
                35                  40                  45
```

-continued

Gly Val Gly Phe Leu Thr Pro Asn Asp Met Ile Ser Arg Leu Val Gly
 50                  55                  60

Phe Ile Asn Arg Lys Ala Glu Asp Ala Gly Val Arg Ser Val Glu Ser
 65                  70                  75                  80

Phe Arg Gln Ile Ser Asp Val Val Leu Ile Val Pro Gln Ile Ala
                 85                  90                  95

Leu Pro Ala Glu Leu Ser Leu Lys Leu Val Asp Ser Ala Asn Ile Leu
            100                 105                 110

Glu Ala Val Asn Asp Gln Glu Val Thr Val Asn Ser Thr Gly Gly Pro
            115                 120                 125

Cys Val Val Met Asn Cys Ala His Ser Ile Pro Asn Glu Asp Arg
130                 135                 140

Thr His Val Asn Gly Ser Glu Val His Arg Arg Leu Gly Ile Gln Tyr
145                 150                 155                 160

Gln Val Asp Cys Asp Asn Ile Ser Gly Arg Val Thr Phe Ser Ile
                165                 170                 175

Thr Ala Leu Trp Arg Glu Ala Phe Ser Phe Arg Pro Ser Phe Tyr Lys
            180                 185                 190

Val Ser Asp Pro Leu Val Val Pro Ile Ser Val Gly Phe Arg Lys Ala
            195                 200                 205

Val Ile Ala Lys Ser His Ala Asp Leu Gln Arg Ser Ile Gly Arg Gly
210                 215                 220

Leu Ile Val Thr His His Ser Ser Gln Ser Ser Val Thr Ser Glu Ser
225                 230                 235                 240

Pro Ile Asp Leu Thr Val Lys Lys Ser Thr Gly Leu Lys Ile Arg Asp
                245                 250                 255

Lys Ser Glu Asp Asp Asn Gln Arg Lys His Pro Val Pro Leu Thr Ser
            260                 265                 270

Ser Asn Asn Lys Leu Lys Thr Leu Arg Val Ser Thr Thr Pro Ile Val
            275                 280                 285

Asn Gly Arg Ser Thr Ser Thr Ser Glu
            290                 295

<210> SEQ ID NO 12
<211> LENGTH: 214
<212> TYPE: PRT
<213> ORGANISM: Citrus Leprosis virus

<400> SEQUENCE: 12

Met Asp Ala Gln Leu Leu Gln Ala Asn Lys Arg Leu Leu Arg Arg Ala
1               5                   10                  15

Ala Asn Val Arg Gln Arg Tyr Lys Met Leu Ala Thr Glu Ser Phe Val
                20                  25                  30

Ala Asp Ile Lys Gln Ile Leu Leu Arg Phe Ile Gln Lys Pro Asn Val
            35                  40                  45

Ile Ile Met Tyr Ile Ser Val Leu Val Leu Phe Ala Ala His Ile Asp
         50                  55                  60

Ser Asn Thr His Asp Ile Leu Asp Asp Leu Ala Ala Gln Phe Pro Asn
65                  70                  75                  80

Asn Thr Phe Ile Glu Trp Ala Lys Ser Asn Phe Phe Arg Ile Cys Gly
                85                  90                  95

Ala Leu Val Phe Ile Pro Val Ile Ile Asp Thr Glu Glu Lys His Arg
            100                 105                 110

Asn Tyr Leu Ala Leu Val Ile Phe Val Phe Leu Met Gly Phe Pro Gln
            115                 120                 125

```
Arg Ser Ile Met Glu Tyr Phe Ile Tyr Ser Ile Ser Phe His Val Tyr
        130                 135                 140

Ala Lys Ala Lys His Pro Val Thr Arg Ile Phe Ile Gly Ala Ala
145                 150                 155                 160

Val Phe Ser Cys Val Met Phe Gly Ile Phe Thr Asn Glu Gln Leu Arg
            165                 170                 175

Lys Leu Tyr Ala Glu Leu Pro Lys Val Pro Thr His Pro Val Ala Val
            180                 185                 190

Asn Arg Val Glu Lys Val Ala Asn Arg Ala Ser Arg Val Ser Thr Glu
            195                 200                 205

Gly Thr Val Asn Phe Gly
    210
```

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acagactacg tgaaatatac c                                              21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtgaaactc cgaatccatt                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaaattgct tcctcacttg                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtgttgtgg taccaccacc                                                20

<210> SEQ ID NO 17
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 17
gtaccgcact tgagcctatc                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aacctcgccc agctgacaac                                                  20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggttgcttta cgttcgagtg tga                                              23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgttgtggag acccagagca                                                  20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtagtgata tcatgtcatg tg                                               22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtacaccac cagctagaag                                                  20
```